(12) United States Patent
Dias et al.

(10) Patent No.: US 9,700,322 B2
(45) Date of Patent: Jul. 11, 2017

(54) MECHANICAL EMBOLIZATION DELIVERY APPARATUS AND METHODS

(71) Applicant: Three Rivers Medical Inc., Mountain View, CA (US)

(72) Inventors: Mark Andrew Dias, San Jose, CA (US); Ricardo Manabat Afan, San Ramon, CA (US); Robert Garabedian, Mountain View, CA (US)

(73) Assignee: Three Rivers Medical Inc., Mountain View, CA (US)

( * ) Notice: Subject to any disclaimer, the term of this patent is extended or adjusted under 35 U.S.C. 154(b) by 0 days.

(21) Appl. No.: 15/293,163

(22) Filed: Oct. 13, 2016

(65) Prior Publication Data

US 2017/0105739 A1   Apr. 20, 2017

Related U.S. Application Data

(60) Provisional application No. 62/241,316, filed on Oct. 14, 2015, provisional application No. 62/348,710, filed on Jun. 10, 2016.

(51) Int. Cl.
*A61M 29/00* (2006.01)
*A61B 17/12* (2006.01)
*A61B 90/00* (2016.01)

(52) U.S. Cl.
CPC .. *A61B 17/12145* (2013.01); *A61B 17/12113* (2013.01); *A61B 90/39* (2016.02); *A61B 2017/12054* (2013.01); *A61B 2090/3966* (2016.02)

(58) Field of Classification Search
CPC .............. A61B 2017/12054; A61B 17/12109–17/12113; A61B 2017/00623; A61B 2017/1205–2017/12095; A61M 25/0138
See application file for complete search history.

(56) References Cited

U.S. PATENT DOCUMENTS

| | | |
|---|---|---|
| 5,108,407 A | 4/1992 | Geremia et al. |
| 5,122,136 A | 6/1992 | Guglielmi et al. |
| 5,263,964 A | 11/1993 | Purdy |
| 5,334,210 A | 8/1994 | Gianturco |
| 5,350,397 A | 9/1994 | Palermo et al. |
| 5,382,259 A | 1/1995 | Phelps et al. |
| 5,895,391 A | 4/1999 | Farnholtz |
| 5,925,059 A | 7/1999 | Palermo et al. |
| 6,113,622 A | 9/2000 | Hieshima |
| 6,203,547 B1 | 3/2001 | Nguyen et al. |
| 6,273,879 B1 * | 8/2001 | Keith ................ A61M 25/0662 600/435 |

(Continued)

FOREIGN PATENT DOCUMENTS

WO    WO2014/107529 A2    7/2014

*Primary Examiner* — Darwin Erezo
*Assistant Examiner* — Lindsey Bachman
(74) *Attorney, Agent, or Firm* — Shay Glenn LLP

(57) ABSTRACT

Mechanical delivery system for neurovascular embolization apparatus and method of use. A mechanical system for delivery of implants, such as coils for endovascular embolization of intracranial aneurysms and other neurovascular abnormalities such as arteriovenous malformations and ateriovenous fistulae, may include a detachment system for the release of a coil that deforms a detent to release (or eject) the implant.

19 Claims, 18 Drawing Sheets

(56) References Cited

U.S. PATENT DOCUMENTS

| | | |
|---|---|---|
| 6,458,137 B1 | 10/2002 | Klint |
| 2002/0165569 A1 | 11/2002 | Ramzipoor et al. |
| 2004/0034363 A1 | 2/2004 | Wilson et al. |
| 2004/0220585 A1 | 11/2004 | Nikolchev |
| 2005/0154417 A1 | 7/2005 | Sepetka et al. |
| 2007/0179520 A1 | 8/2007 | West |
| 2007/0299461 A1 | 12/2007 | Elliott |
| 2009/0138023 A1 | 5/2009 | Johnson et al. |
| 2010/0174269 A1 | 7/2010 | Tompkins et al. |
| 2010/0314031 A1 | 12/2010 | Heideman et al. |
| 2011/0295303 A1 | 12/2011 | Freudenthal |
| 2012/0041472 A1* | 2/2012 | Tan ............ A61B 17/12113 606/200 |
| 2013/0053884 A1* | 2/2013 | Roorda ........ A61B 17/0057 606/232 |
| 2013/0178889 A1* | 7/2013 | Miles .......... A61B 17/12122 606/200 |
| 2014/0058434 A1* | 2/2014 | Jones ........... A61B 17/1214 606/200 |
| 2014/0142621 A1* | 5/2014 | Masters ....... A61B 17/12109 606/213 |

* cited by examiner

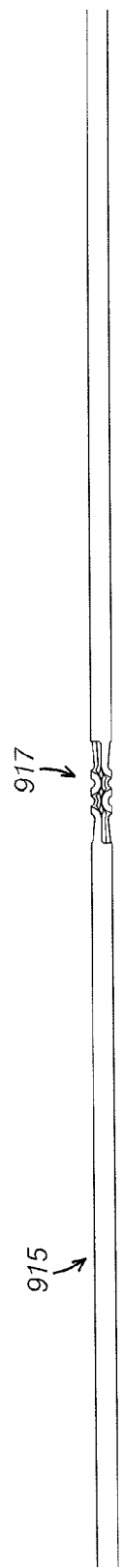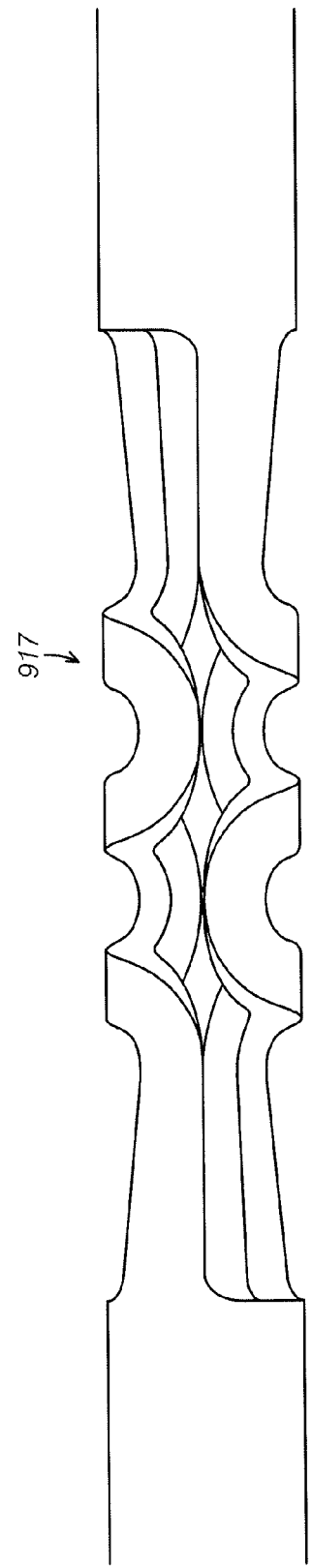
FIG. 10A
FIG. 10B

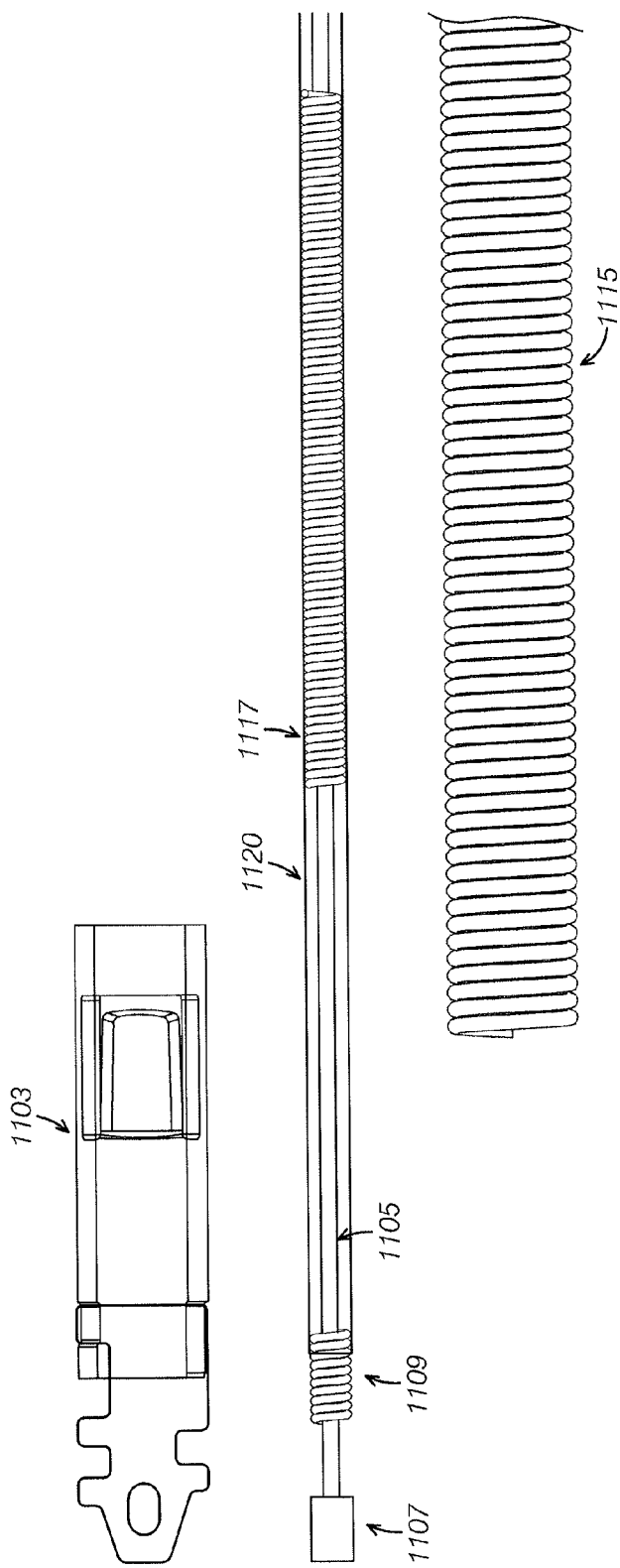
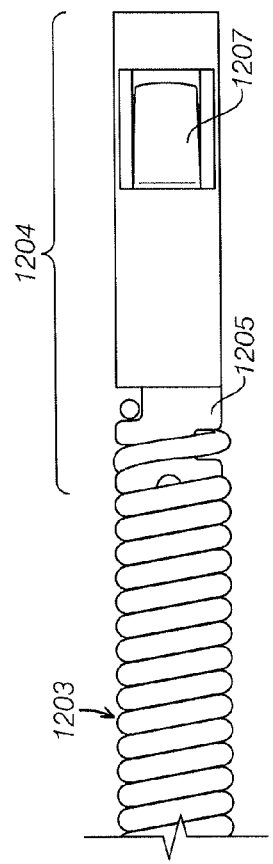
FIG. 11
FIG. 12

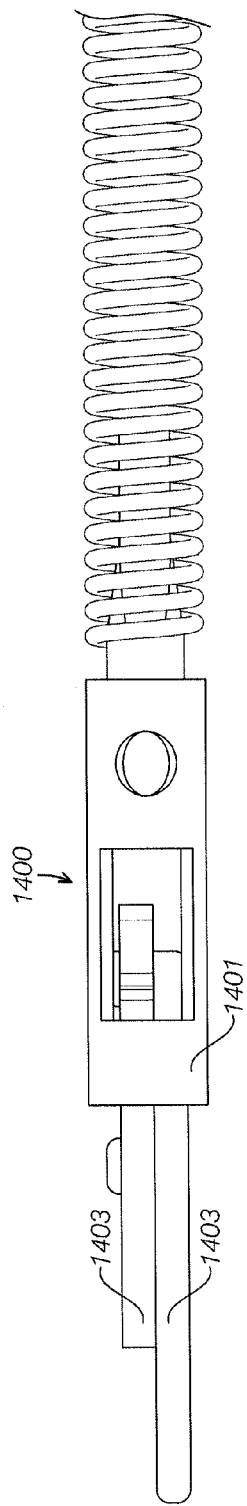
FIG. 14A
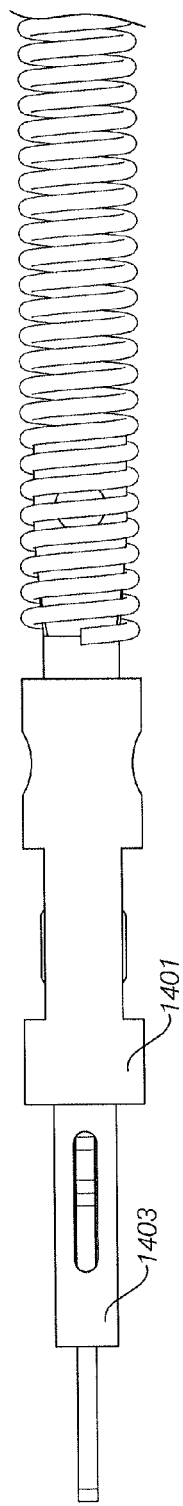
FIG. 14B
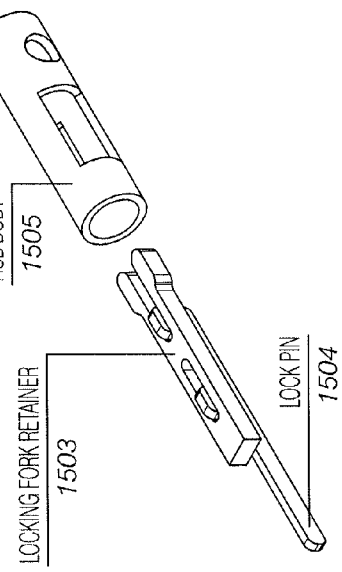
FIG. 15C
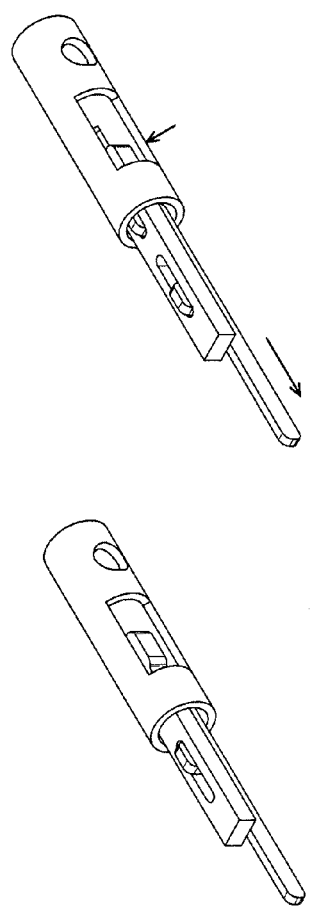
FIG. 15B
FIG. 15A Detent 1604

1606

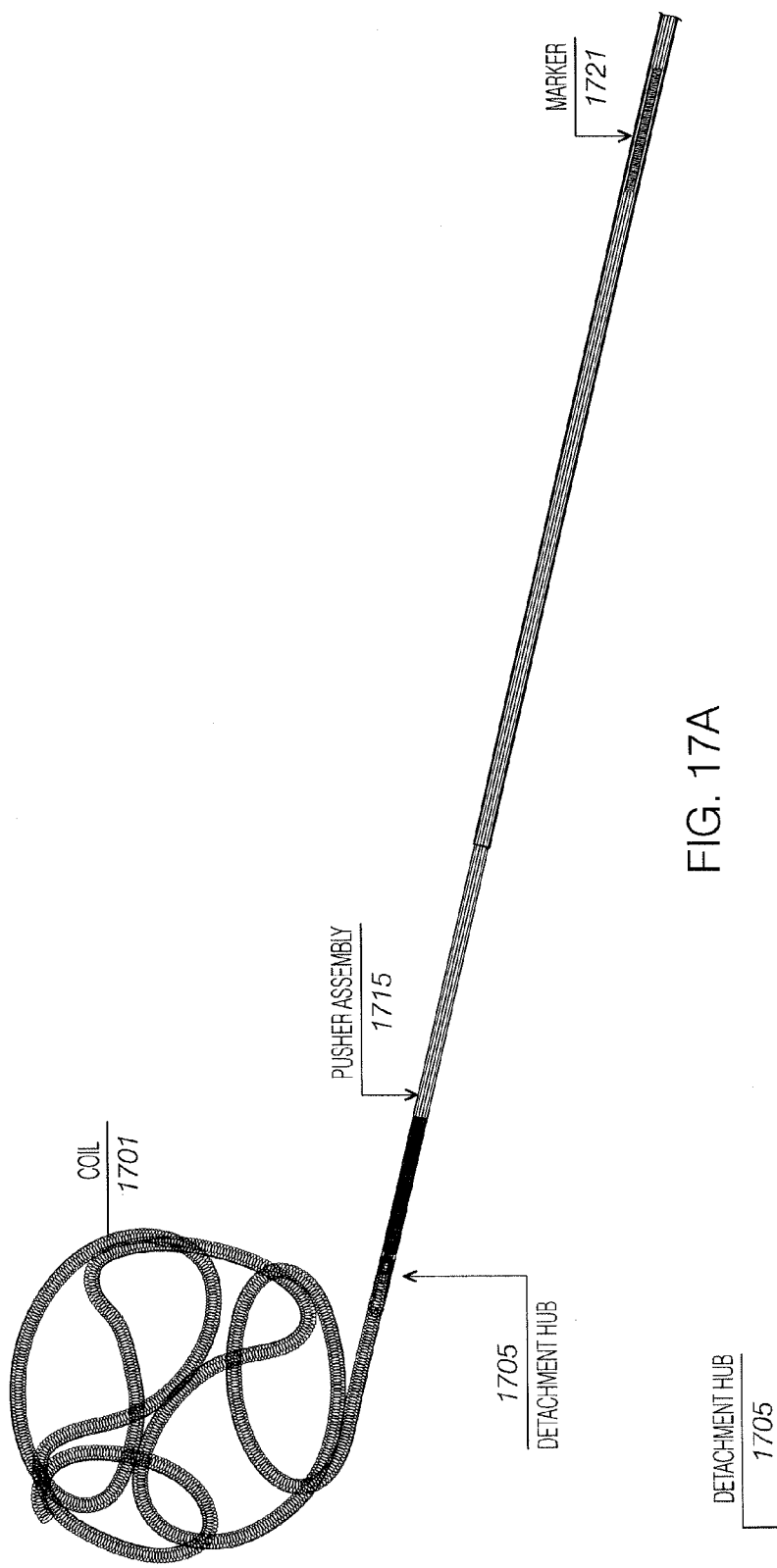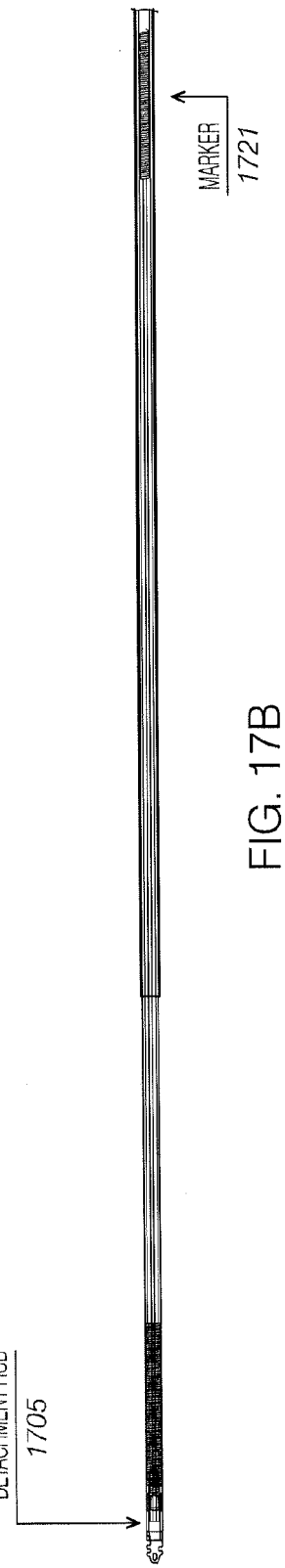
FIG. 17A
FIG. 17B

MECHANICAL EMBOLIZATION DELIVERY APPARATUS AND METHODS

CROSS REFERENCE TO RELATED APPLICATIONS

This patent application claims priority to U.S. Provisional Patent Application No. 62/241,316, titled "MECHANICAL EMBOLIZATION DELIVERY APPARATUS AND METHODS" filed on Oct. 14, 2015 and U.S. Provisional Patent Application No. 62/348,710, titled "MECHANICAL EMBOLIZATION DELIVERY APPARATUS AND METHODS" filed on Jun. 10, 2016, each of which is herein incorporated by reference in its entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Mechanical delivery apparatuses and methods for neurovascular implants.

BACKGROUND

Described herein are medical devices for placing an implant such as an embolic device at a predetermined site within a vessel or lumen of a human (or animal) body. For example, described herein are catheter-based deployment apparatuses for delivering an embolic device such as a coil. These apparatuses are particularly suited to transport an embolic device, such as an embolic coil, through the vasculature of the human brain to a selected site within the vessel or within an aneurysm, and may address many of the problems identified with prior art systems, as will be briefly described below.

For many years, flexible catheters have been used to place various devices within the vessels of the human body. Such devices may include dilation balloons, radiopaque fluids, liquid medications, and various types of occlusion devices such as balloons and embolic coils. Examples of such catheter-based devices are disclosed in U.S. Pat. No. 5,108,407, entitled, "Method and Apparatus for Placement of an Embolic Coil" and U.S. Pat. No. 5,122,136, entitled, "Endovascular Electrolytically Detachable Guidewire Tip For The Electroformation Of Thrombus In Arteries, Veins, Aneurysms, Vascular Malformations And Arteriovenous Fistulas." These patents disclose catheter-based devices for delivering embolic coils to preselected positions within vessels of the human body in order to treat aneurysms, or alternatively, to occlude blood vessels at a particular location.

Coils which are placed in vessels may take the form of helically wound coils, or alternatively, may take the form of randomly wound coils, coils wound within coils or other such coil configurations. FIGS. 1 and 2 illustrate examples of coils that may be used; such coils may have complex and helical shapes to accommodate a broad range of patient anatomy. For example, coils may have a complex frame of about 2 mm×3 cm to 15 mm×50 cm (e.g., 1 mm×2 cm to 5 mm×10 cm). Coils may be made ultra soft, soft or standard flexibility and, may include a Polymer or metallic Stretch Resistant (SR) Member. Other examples of various coil configurations are disclosed in U.S. Pat. No. 5,334,210, entitled, "Vascular Occlusion Assembly" and U.S. Pat. No. 5,382,259 entitled, "Vasoocclusion Coil with Attached Tubular Woven or Braided Fibrous Covering." Embolic coils are often formed of a radiopaque metallic material, such as platinum, gold, tungsten, or alloys of these metals. Several coils may be placed at a given location to occlude the flow of blood through the vessel, or aneurysm, by promoting thrombus formation at the particular site.

In the past, embolic coils have been placed within the distal end of a catheter. When the distal end of the catheter is properly positioned, the coil may then be pushed out of the end of the catheter with a pusher member to release the coil at the desired location. This procedure for placement of an embolic coil may be conducted under fluoroscopic visualization such that the movement of the coil through the vasculature of the body may be monitored and the coil placed at the desired location.

In some procedures, glue or solder may be used to attach a coil to a guidewire, which in turn, is placed within a flexible catheter for positioning the coil within the vessel at a preselected position. Once the coil is in the desired position, the coil is held in position by the catheter and the guidewire is pulled proximally to thereby cause the coil to become detached from the guidewire and released from the catheter. Such a coil positioning system is disclosed in U.S. Pat. No. 5,263,964 entitled, "Coaxial Traction Detachment Apparatus and Method."

Still another coil positioning procedure is that of having a catheter with a socket at the distal end of the catheter for retaining a ball which is, in turn, bonded to the proximal end of the coil. The ball, which is generally larger in diameter than the outside diameter of the coil, is placed in the socket within the lumen at the distal end of the catheter and the catheter is then moved into a vessel in order to place the coil at a desired position. Once the position is reached, a pusher wire with a piston at the end thereof is pushed distally from the proximal end of the catheter to push the ball out of the socket in order to release the coil at the desired position. Such a system is disclosed in U.S. Pat. No. 5,350,397, entitled, "Axially Detachable Embolic Coil Assembly." A similar prior art apparatus is shown in FIG. 3, which is described in U.S. Pat. No. 5,895,391, titled "Ball Lock Joint and Introducer for Vaso-Occlusive Member". In this example, an interference wire is used to drive the large ball attached to the end of the coil into a retaining seat on the device. Once the distal end of a delivery catheter is positioned at a target site, the vaso-occlusive device 222 is engaged within a holding member 226 and is inserted and forwarded to the chosen target site in the body. The interference wire 228 is in such a position during this introductory step so that the whole assembly may be forwarded through the catheter as an assembly. Once positioned, the interference wire is removed and the catheter, holding member, and interference wire are each withdrawn from the body.

Another procedure for placing an embolic coil within a vessel is that of using a heat releasable adhesive bond for retaining the coil at the distal end of the catheter. One such system uses laser energy transmitted through a fiber optic cable to apply heat to the adhesive bond in order to release the coil from the end of the catheter. Such a procedure is disclosed in U.S. Pat. No. 5,108,407, entitled "Method and Apparatus for Placement of an Embolic Coil."

Yet another coil deployment system incorporates a catheter having a lumen throughout the length of the catheter and a distal tip for retaining the coil for positioning the coil at a preselected site. The distal tip of the catheter is formed of a material which exhibits the characteristic that when the lumen of the catheter is pressurized the distal tip expands radially to release the coil at the preselected site. Such a deployment system is disclosed in U.S. Pat. No. 6,113,622, entitled, "Embolic Coil Hydraulic Deployment System."

Still another coil deployment system incorporates an interlocking mechanism on the coil. The interlocking end on the embolic coil couples with a similar interlocking mechanism on a pusher assembly. A control wire which extends through the locking mechanism secures the coil to the pusher assembly. The pusher assembly and embolic coil are initially disposed within the lumen of a catheter. When the embolic coil is pushed out of the end of the catheter for placement, the control wire is retracted and the coil disengages from the pusher assembly. Such a deployment system is disclosed in U.S. Pat. No. 5,925,059, entitled, "Detachable Embolic Coil Assembly."

Yet another coil deployment system incorporates an embolic device detachably mounted on the distal portion of a pusher member and held in place with a connector thread or fiber. The fiber passes through a cutter member that may be activated to cut the connector fiber. Once the connector fiber is cut, the embolic device is released. Such a deployment system is disclosed in Published U.S. Patent Application Publication No. 2002/0165569, entitled, "Intravascular Device Deployment Mechanism Incorporating Mechanical Detachment."

Another coil deployment system incorporates an embolic device with a stretch resistant member therethrough. The distal end of the stretch resistant member attaches to the embolic coil and the proximal end of the stretch resistant member is detachably mounted on the pusher member through various means such as adhesive, or by a connector fiber adhered to or tied to the pusher member, and is detachable by the application of heat. Such a deployment system is disclosed in U.S. Patent Application Publication No. 2004/0034363, entitled, "Stretch Resistant Therapeutic Device."

Still another coil deployment system incorporates a pusher wire with a stiff wavy-shaped end segment which is coupled to the embolic coil and is placed in the lumen of the catheter. The coil is advanced through the catheter until it reaches a predetermined site in the vessel at which time the pusher wire is retracted and the embolic coil is released. Such a system is disclosed in U.S. Pat. No. 6,203,547, entitled, "Vaso-occlusion Apparatus Having A Manipulable Mechanical Detachment Joint And A Method For Using The Apparatus."

The various deployment systems described above may all be used to deliver one or more implants to a target site, but each of these systems may be improved. In particular, for non-mechanical systems (e.g., electrical, chemical or hydraulic release systems, the response time of actuating is delayed, which may lead to error and frustration on the part of the surgeon. Many of the mechanical delivery systems described herein also suffer from problems associated with the reliability and robustness of the apparatus and method of operation. Further, implants that are mechanically releasing implants from known systems may not be released with sufficient force, and may require direct visualization to confirm release. Described herein are methods and apparatuses that may address these deficiencies.

SUMMARY OF THE DISCLOSURE

Described herein are mechanical delivery apparatuses for neurovascular implants (including embolization implants) and method of use. These apparatuses may include devices and systems. For example, described herein are mechanical system for delivery of implants such as embolic coils for endovascular embolization of intracranial aneurysms and other neurovascular abnormalities such as arteriovenous malformations and arteriovenous fistulae. Any of these apparatuses may include a deformable detachment zone that is coupled to the implant, and delivered with the implant. Although the apparatuses and methods described herein are typically described in the context of embolic coil release, these apparatuses and methods may be used to deliver any implant of appropriate scale (e.g., approximately the size/dimensions of an embolic coil), including but not limited to filters, baskets, plugs, supports (e.g., stents), braids (e.g., expandable braids), and the like.

Any of these apparatuses may be used with a delivery or guide catheter ("guiding catheter" or "delivery catheter") which may include a marker at or near its distal end. The delivery catheter may be a micro catheter ("micro catheter"). As will be described in greater detail below, the apparatuses described herein for delivery of an implant by mechanical detachment may include a detachable delivery wire assembly (DDW), which may be disposable or reusable, and may include a proximal hypotubing body and a distal polymer jacketed coil (outer pusher assembly), and an inner pull wire with an enlarged distal end for engaging a detachment hub assembly. The DDW may also be referred to as a pusher assembly (and may include the outer pull assembly and the inner pull wire). The DDW or pusher assembly may be used with an implant (e.g., embolic coil) connectable or pre-connected to a detachable delivery wire via a hub assembly (detachment hub or detachment hub assembly), and a detachment handle (handle). The implant and detachment hub assembly may be pre-connected or pre-loaded onto the enlarged distal end of the pull wire of a DDW.

For example, in one variation, the apparatus is configured as a vascular embolization coil system that includes: an implant (e.g., coil) that is pre-attached to a detachable delivery wire assembly (DDW) via a hub assembly (e.g., a detachment hub assembly), and, optionally, a detachment handle (DH). The detachable delivery wire or pusher assembly may include an outer pusher assembly (e.g., outer coils and/or hypotubes having sufficient column strength to push the implant distally and/or pull it proximally), an inner pull wire assembly including an inner pull wire for deployment/release, an enlarged tip at the distal end of pull wire, and a centering coil near the distal end of the pull wire to keep the detachment hub assembly aligned concentrically with the distal end of the DDW. The DDW may also include a marker (visible under fluoroscopy) region on the pull wire, which moves with the pull wire; for example, the pull wire moves proximally within the outer pusher assembly when the pull wire is actuated to release the implant. The DDW may also include a lubricious cover (e.g., lubricious jacket) which may at least partially cover the pull wire (e.g., the distal or a middle region of the pull wire), centering coil and/or marker, to reduce sliding friction when the pull wire moves proximally within the DDW. Optionally, the DDW (e.g., the outer pusher assembly of the DDW) may also include a proximal strain relief region. In general, the inner pull wire may be coupled (e.g., by friction fitting, pinching, etc.) to the outer pusher assembly, so as to keep tension on the pull wire at the distal end of the DDW. This tension may help keep the detachment hub and any attached implant snugly against the distal end of the DDW, but may be readily overcome by pulling the internal pull wire distally (from the proximal end of the DDW) to release/eject the implant.

As mentioned, any of these apparatuses may also include a handle, including an actuating handle having hand/finger controls for applying force (e.g., between about 20-500 g of force, e.g., between 20-400 g, between 20-300 g between 20-150 g, between 20-125 g, between 20-100 g, etc.) to pull the pull wire proximally, overcoming the friction within the DDW, deforming the deformable mechanical trap and releasing the implant (connected to the hub assembly). The component devices may be provided sterile and nonpyrogenic (e.g., for use with a single patient).

As mentioned, the apparatuses described herein may be used with any appropriate implant, including, in particular, vascular coils such as embolization coils. The implant may be delivered to the targeted vessel location under fluoroscopy and standard endovascular technique using a commercially available micro catheter (MC), as will be described in greater detail below, the implant (e.g., coil) may then be mechanically detached from the detachable delivery wire using the handle (DH). Deployment of the apparatuses described herein may be particularly effectively and easily visualized to confirm delivery/detachment of the implant.

For example, a coil may be a bare platinum alloy; coils are available in different shapes, diameters and lengths to accommodate a range of targeted vessel sizes. In the examples described herein, a filament is included in the central lumen of the coil to prevent stretching of the Coil during insertion and retrieval manipulations of the coil.

In general, the implant is attached (typically permanently, although temporary, removable, and/or degradable attachments are also contemplated) to a detachment hub assembly. A detachment hub assembly (also referred to as simply a hub assembly or HA) is a mechanical element that may be connected on a proximal-most end of the implant (e.g., coil) and may link the implant to the DDW detachment system. The detachment hub assembly may be pre-attached to coil and to the accompanying detachment system of the DDW as will be described in greater detail below. The detachment hub assembly may include two or more portions that are connected together, including an implant coupler (also referred to as an adapter, coil adapter or coil coupler) and a deformable mechanical release (also referred to as a tab or release tab). The deformable mechanical release typically includes one or more (e.g., two, three, four, etc.) deformable detents within the deformable mechanical release, forming a trap lumen into which the distal end of the pull wire may be held. For example, the deformable detents may be projections such as tabs, bumps, bars, the like, into this lumen, which are configured or adapted to be deformed (e.g., outwards) when an applied force (e.g., when pulling the pull wire proximally) exceeds a predetermined threshold (e.g., greater than 20 grams of force, greater than 30 grams of force, greater than 40 grams of force, greater than 50 grams of force, greater than 60 grams of force, greater than 70 grams of force, between 20-500 grams of force, between 50-200 grams of force, between 50-500 gf, between 20-400 gf, between 20-250 gf, between 20-200 gf, etc. and release the distal end of the pull wire from within the trap lumen and therefore the hub assembly. Thus, the deformable detents of the hub assembly (e.g., deformable mechanical release) may hold (under tension) the distal end of the pull wire of the detachable deliver wire (DDW), which may have an enlarged diameter and/or a proximal neck region of smaller diameter than the distal end region, so that the distal end region of the pull wire may be secured within the deformable mechanical release by the deformable detents; when adequate force is applied to pull the pull wire proximally, the distal end of the pull wire may deform the deformable detents, allowing the distal end of the pull wire to be pulled proximally out of the deformable mechanical release and ejecting the implant (and attached hub assembly) distally. Because the hub assembly coupled to the implant is pulled proximally against the distal end of the DDW, when the deformable detents finally deform and release the distal end of the pull wire from the hub assembly, the hub assembly and implant may be released distally with a force moment that drives the implant (and attached hub assembly) distally away from the DDW.

In some variations the hub assembly does not include a separate hub coupler (implant coupler/adapter) and deformable mechanical release; a single piece may perform both functions. For example, the implant (e.g., coil) may be coupled directly to the hub assembly and the same hub assembly piece may include a trap lumen with one or more deformable detents. The hub assembly is generally coupled directly and strongly (e.g., by crimping and/or welding and/or cementing) to the implant.

In general, the detachable delivery wire (DDW) is an elongate assembly that includes the pull wire within an inner lumen of the DDW. The enlarged distal end of the pull wire (or the region distal to a neck region) may be a ball, cylinder, or the like, and may be pre-loaded into the trap lumen of the hub assembly. The DDW also typically includes an outer pusher assembly having an inner lumen in which the pull wire resides. The pusher assembly may be formed of a hypotube or hypotubes, a coil or coils, a polymer tube or tubes, a braid or combinations of these, including serial and parallel arrangements of these. For example, the DDW may be formed of a distal coil region that may be jacketed (e.g., proximal to the distal end to increase the softness/flexibility of the distal end). Distal to the distal coil region may be a marker coil region (concentric coils or hypotube regions may be included as well, to adjust the overall stiffness/flexibility of the DDW). The proximal end of DDW may include a proximal hypotube. In some variations the proximal region may also include a strain relief hypotube, which may include a laterally elastic region, such as a spring region. The pull wire may be held (e.g., by a crimp, friction hold, internal detent, adhesive, etc.) within the pusher assembly so that the distal portion of the pull wire is in tension, pulling the hub assembly and attached implant against the distal end of the DDW. The strain relief hypotube may allow the tension on the distal end of the pull wire while still allowing the DDW to be flexible and bendable. The distal end of the DDW may be adapted to fit flush against the proximal end of the hub assembly. The DDW may be made of stainless steel and jacketed with a medical grade polymer. As mentioned, the DDW may include one or more marks, such as a safety marker, e.g., fluoro safety marker, or other visible marks, on the proximal shaft of the pusher assembly that provides a visual indication of when the implant (e.g., coil) is approaching but not exiting the distal end of the MC. In some variations the fluoro safety marker is on the proximal region of the shaft of the DDW and allows the user to see when an implant (e.g., coil) is approaching the distal end of a delivery catheter (e.g., microcatheter). The safety marker may, in some variations, be visualized with the naked eye or provide tactile feel. For example, a safety marker may include one or more colored region, such as one or more pieces of colored heat shrink material that is applied to the outside of the proximal stainless shaft.

As described in greater detail herein, any of the apparatuses described herein may also include one or more additional markers, such as detachment markers, or "3 cm markers" on the pull wire. This pull wire marker may be a coil that is fixed to the internal delivery/pull wire inside the lumen of the DDW is only visible under live fluoroscopy. It may have a very specific position towards the very distal end of the DDW, e.g., approx 30 mm proximal to the distal tip of the DDW. As mentioned, any of the DDWs described herein may also include a lubricous cover (e.g., jacket, coating, layer, sleeve, etc.) that covers at least a portion of the pull wire and/or markers (e.g., the centering coil and the 3 cm marker). This lubricious cover (referred to here as a lubricious jacket) may reduce internal friction when the pull wire is pulled proximally within the DDW. The lubricous jacket may be constructed from an extrusion, or shrink tubing, a deposition or spray process or a lubricant or coating. When the detachment handle is actuated, releasing the implant (e.g., by deforming the one or more detents in the hub assembly), the resulting motion will pull the internal pull wire proximally, and this movement can be visualized by motion of the 3 cm marker under live fluoroscopy and may be used to confirm detachment has taken place, as will be discussed in greater detail with respect to FIGS. 5A-5C, 5D-5F and 19A-19B, below.

In use, deforming the detents in the hub assembly releases the implant and hub assembly. For example, an apparatus may be configured to release a coil (e.g., a vasoocclusive coil) for vascular occlusion of blood vessels within the neurovascular system to permanently obstruct blood flow to an aneurysm or other vascular malformation and for arterial and venous embolizations in the peripheral vasculature. These apparatuses may be used for controllable delivery of implants including vasoocclusive devices to a selected site within the vasculature or other lumen of a human body by the use of a catheter.

Also described herein are apparatuses that include a hub assembly that is coupled to an implant such as a coil (e.g., vasoocclusive coil) at a distal end and proximally may couple with a distal end of a pull wire that has been connected to a locking fork retainer. The locking fork retainer typically includes two (or more) arms that are compressible when radially-inwardly directed force is applied, reducing the diameter of the locking fork retainer. A lock (also descriptively referred to in some variations as an axial sliding lock or simply sliding lock) may include a locking projection (e.g., tab, etc.) that is positionable between the arms of the locking fork retainer, preventing the arms of the fork from bending inward. By sliding the lock proximally (or distally), the locking projection may be removed or displaced from between the fork arms, allowing the arms to bend inwards. In some variations the axially sliding lock member is coupled to a pull wire so that when sufficient pulling (proximally pulling) force is applied to the pull wire, the axial sliding lock is pulled proximally from out of the distal regions between the arms of the locking fork retainer; the axial sliding lock is also coupled with the locking fork retainer so that once the locking fork retainer is slid proximally, the pulling force then pulls the locking fork retainer proximally. When the locking fork retainer if held within the hub assembly, the arms of the locking fork retainer may be driven inwardly as force from the pull wire may pull the locking fork retainer against the hub assembly (e.g., against one or more ramp surfaces); reducing the diameter of the locking fork retainer arms may then permit them to be released proximally out of the hub assembly and release the implant and hub assembly. The DDW in this embodiment may be otherwise similar to the DDW described above, however the distal end of the pull wire may be secured to the lock. Any of the locks (axial sliding locks) described herein may also include a mechanical resistance, including a deformable detent that must be overcome first, before the axial sliding lock may be pulled proximally. For example, in any of the variations described herein, the pull wire and/or in some variations, the axial sliding lock, may be crimped to the distal end region of the pusher assembly. To actuate the device, the pulling force must apply sufficient force necessary to overcome the crimp, and (in this example) slide the lock proximally, and driving collapse of the fork arms, releasing the hub assembly and implant.

Thus, in general, any of the apparatuses described herein may include a hub assembly coupled to an implant (such as a vasoocclusive coil), and a detachable delivery wire (DDW). The detachable delivery wire may include an outer pusher assembly and an inner pull wire within a lumen of the pusher assembly. The distal end of the pull wire is initially coupled to the hub assembly (e.g., a trap lumen having deformable detents and/or an axial sliding lock coupled to a locking fork retainer), and a more proximal portion of the pull wire is releasably secured within the pusher assembly by a mechanically releasable hold, e.g., by crimping, friction hold, etc. such that if the pull wire is pulled proximally with a force greater than a release force (which may be a predetermined force, e.g., between 50-500 gf), the pull wire will deform the releasable hold, and actuate the release of the hub assembly and implant from the apparatus. The pull wire will then be drawn proximally.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 6A the hub body is shown with the detents engaged to secure ("trap") an enlarged distal end of a pull wire (not shown), while in FIG. 6B the detents are disengaged.

In FIG. 6C the body includes a single detent that is not engaged.

In FIG. 8C, compared to FIG. 8B, the deformable mechanical release portion is transparent to show capture of the distal end of the pull wire.

FIG. 10A is a perspective view of a strain relief region of a DDW.

FIG. 10B is an enlarged view of a spring portion of the strain relief region.

FIG. 11 shows an exploded view of a distal end of a detachable delivery wire and hub assembly such as the one shown in FIGS. 8A-8D, including a 30 mm fluoro marker attached to the pull wire, and a lubricious jacket covering the pull wire, centering coil and marker FIG. 12 shows a hub assembly coupled to an implant (in this example, a vasoocclusive coil).

FIGS. 13A-17B illustrate another example of an apparatus as described herein.

FIG. 13A shows an implant (coil) coupled to a hub assembly that is in turn coupled to a locking fork retainer. The locking fork retainer is locked by an axial sliding lock which may couple to a pull wire of a DDW (not shown).

FIGS. 14A and 14B show top and side views, respectively, of the apparatus of FIGS. 13A and 13B.

FIGS. 15A-15C illustrate operation of a locking fork retainer and hub assembly (before, during and after, disengaging, respectively) such as the one shown in FIGS. 13A-13B, releasing a hub assembly (and any implant attached thereto).

FIGS. 17A-17C illustrate another example of a system including an implant (vasoocclusive coil) coupled to a hub assembly, a detachable delivery wire (DDW), including an outer pusher assembly and an inner pull wire, and a delivery catheter. FIG. 17A shows the implant (coil) coupled to a detachment hub that is connected to a pull wire of a pusher assembly (DDW). FIG. 17B shows the detachment hub coupled to the DDW without the coil attached.

FIG. 17C shows a distal end of a delivery catheter that may be used with a pusher assembly (DDW) and implant.

DETAILED DESCRIPTION

Described herein are mechanical delivery apparatuses and methods of using them to deliver neurovascular implants. In general, these mechanical delivery apparatuses may deliver quickly and may reliably release an implant (such as a vasoocclusive coil) from the delivery apparatus. This may ensure that the implant is released with minimal force so that the implant is not partially left in a vessel or neck of an aneurysm when filling the aneurysm. These apparatuses typically require a mechanical deformation (e.g., of a release or trap detent) to release and eject the implant.

Figure 1:
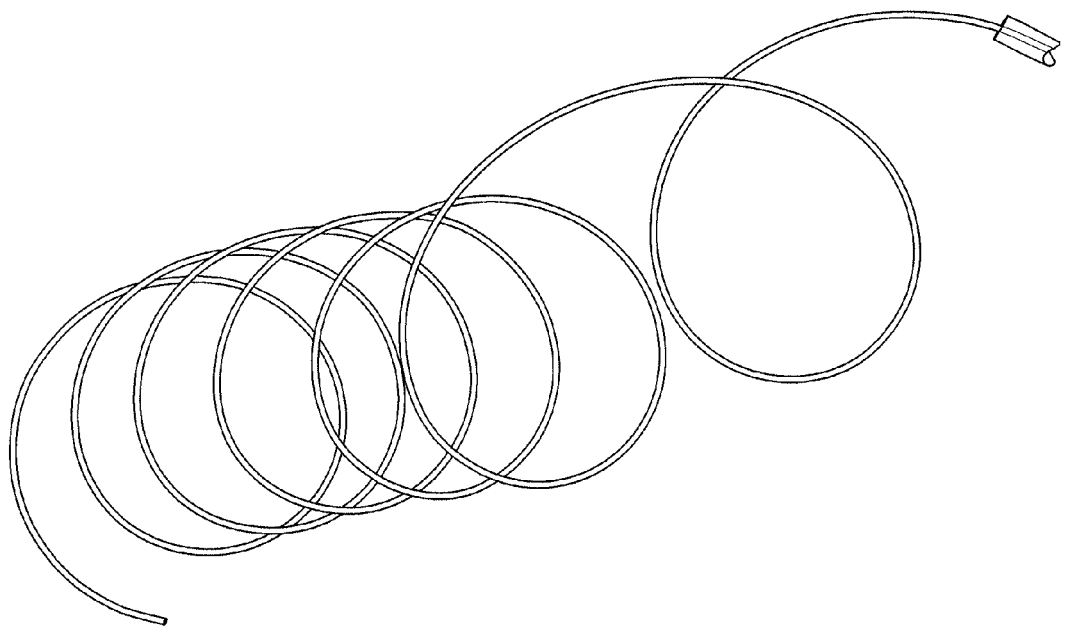
FIGS. 1 and 2 are examples of implants, and particularly of vasoocclusive coils, that may be used with any of the apparatuses described herein.
Figure 2:
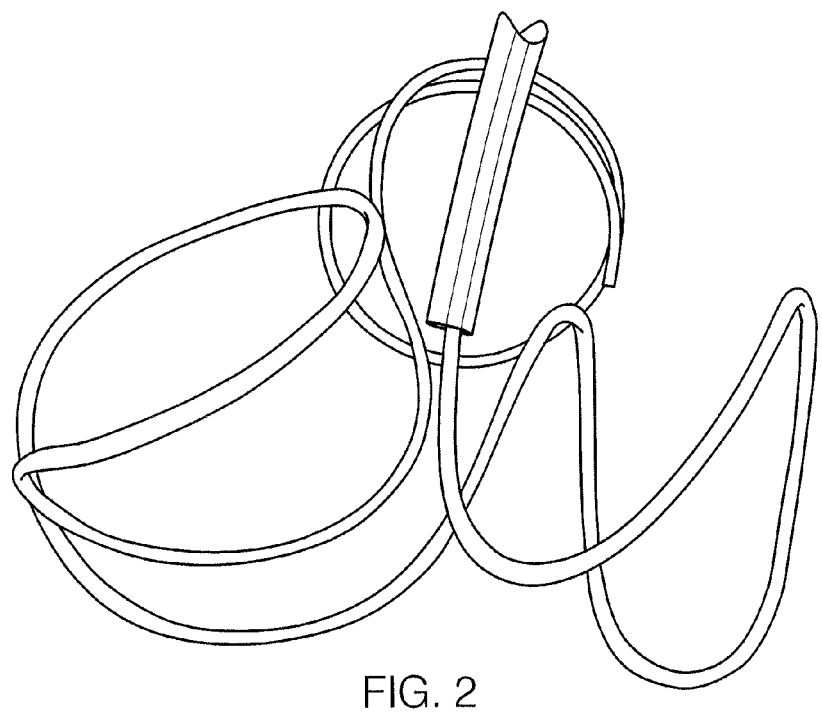
Figure 3:
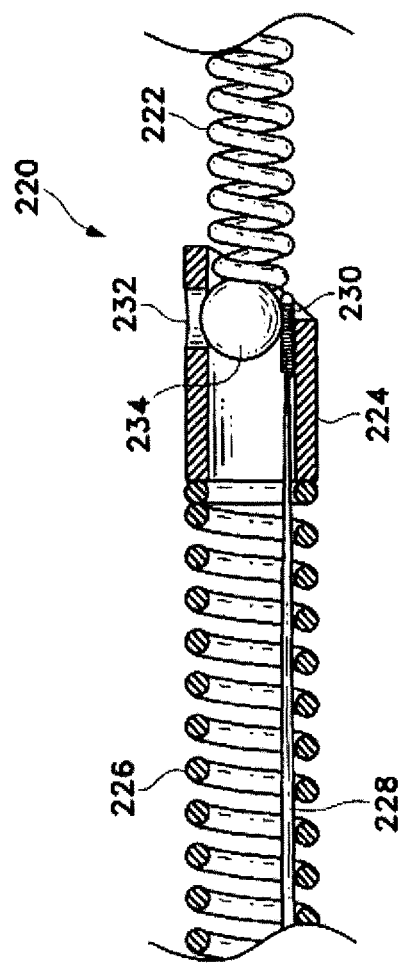
FIG. 3 is an example of a prior art mechanical delivery apparatus for delivering a coil.
Figure 4:
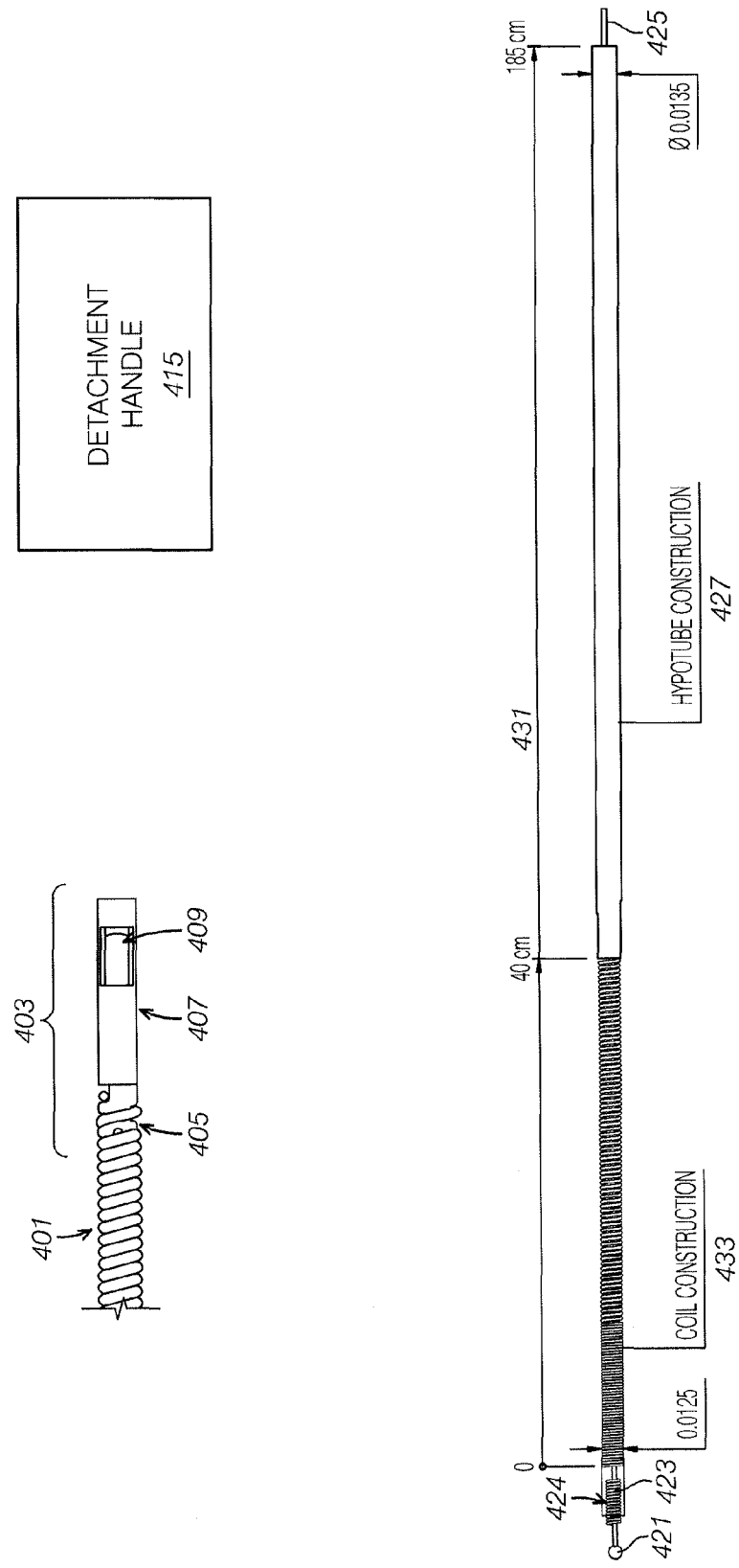
FIG. 4 is an example of an apparatus (shown as a system) including an implant coupled to a hub assembly, detachable delivery wire (DDW) including an outer pusher assembly and an inner pull wire, and a detachment handle configured to couple to the proximal end of the pull wire.

For example, FIG. 4 shows one example of a system as described herein. In this example, the system includes an implant 401 (shown as a coil) affixed (permanently) to a hub assembly 403. The hub assembly includes an implant coupler (implant adapter) 405 to which the proximal end of the coil is affixed. The implant coupler is also permanently connected to the deformable mechanical release (trap) 407. The deformable mechanical release includes an inner trap lumen into which one or more deformable detents 409 project. As will be described below, the distal end of the pull wire may have an enlarged outer diameter (compared to a slightly proximal neck region) and may be retained within the trap lumen until the force applied to pull the pull wire proximally can cause the deformable detents to deform (e.g., bending outwards), releasing the pull wire, and releasing the implant and attached hub assembly.

FIG. 4 also shows a mechanical detachable delivery wire (DDW) 431, with exemplary dimensions. In this example, the distal end 421 of the pull wire 425 is an enlarged region (shown here as a ball, though it may have any appropriate shape (e.g., cylinder, triangular, etc.). The pull wire may also include a centering coil 423 helping to concentrically align the deformable mechanical release 407 with the outer pusher assembly of the DDW 431. The outer assembly of the DDW in this example includes a relatively soft distal end region 433 and a more proximal hypotube region 427. As will be described in greater detail here, the pull wire may also have a fluoro marker attached, e.g., within 50 mm of the distal end (e.g., approximately 30 mm from the distal end) of the pull wire (not shown) and a lubricious jacket 424 covering the centering coil and flouro marker. The pull wire may be releasably secured within the DDW (not shown) to maintain tension on the pull wire and hold the implant and hub assembly against the distal end of the DDW when the pull wire is attached to the hub assembly. The DDW may also include a strain relief region (not shown in FIG. 4) to improve flexibility even when the pull wire is held in tension within the pusher assembly.

Figure 18A:
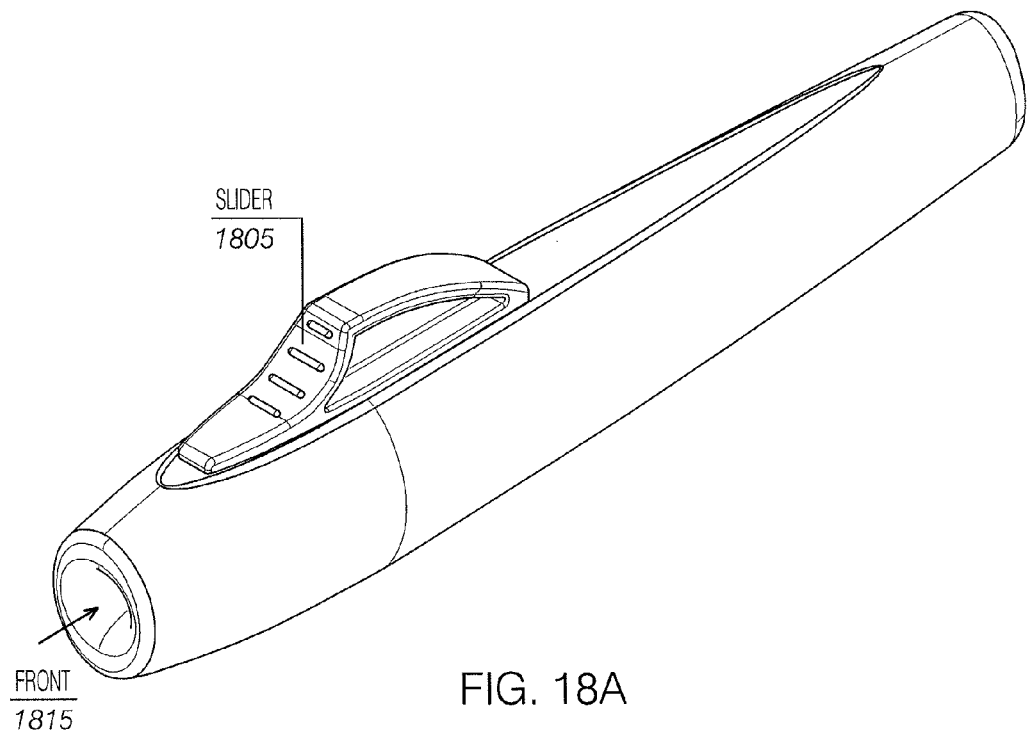
FIG. 18A shows one example of a handle that may be used with a pusher assembly (DDW) to deliver an implant coupled to a detachment hub as described herein.
Figure 18B:
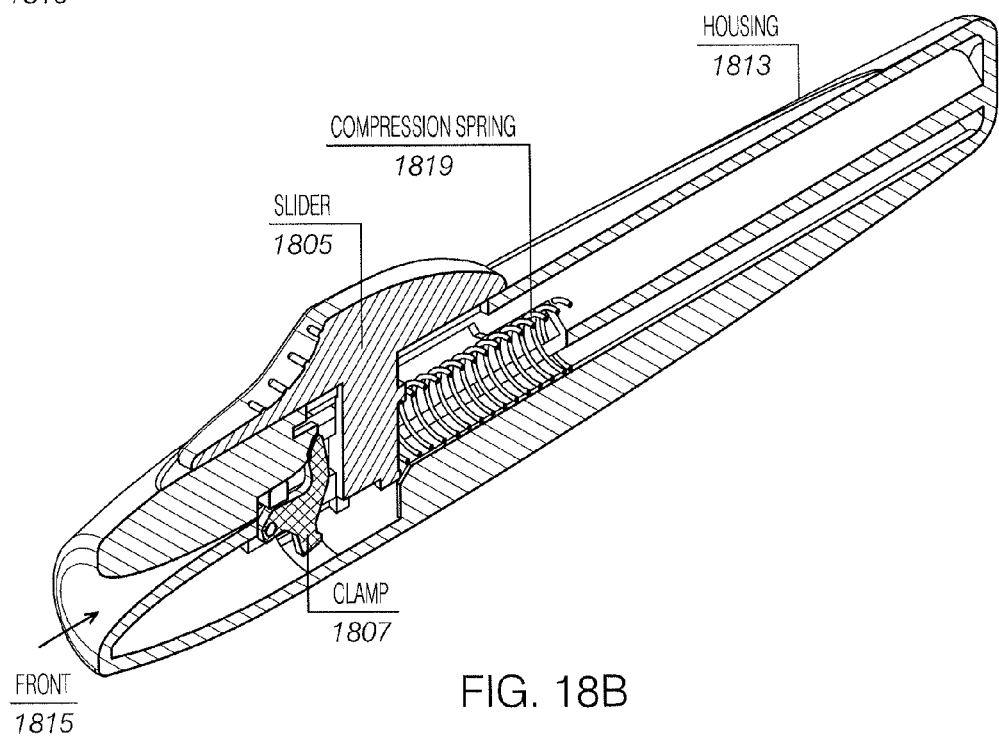
FIG. 18B is transverse section through the delivery handle of FIG. 18A.

A detachment handle is also shown schematically in FIGS. 18A-18B. In general, a detachment handle may be configured to engage the proximal end of the pull wire to allow the pull wire to be actuated (pulled) with by hand to mechanically deform and release (expel) the implant from the apparatus.

Figure 5A:
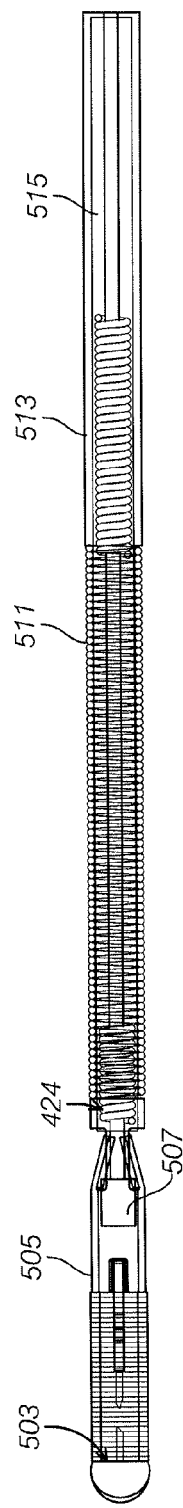
FIGS. 5A-5C illustrate actuation of an example of an apparatus similar to the one shown in FIG. 4. These images also slow the internal 30 mm fluoro marker in initial (pre-detachment, FIG. 5A) and final (post detachment, FIG. 5C) positions.

FIGS. 5A-5C and 5D-5F show examples of an apparatus similar to the apparatus shown in FIG. 4, including an implant 503 coupled to a hub assembly 505. In FIG. 5A, the distal end of the pull wire 507 is trapped in the trap lumen of the hub assembly by two deformable detents and the implant and hub assembly are held against the distal end of the DDW 511 by tension on the pull wire. For example, the pull wire may be crimped or otherwise releasably secured to the pusher assembly of the DDW (not shown), e.g., near the proximal end. In FIG. 5A (which may not be to scale) an example of a marker 513 on the pull wire (in this example, a 30 mm fluoro marker) and lubricious jacket 515 are shown attached to the pull wire within the DDW.

Figure 5B:
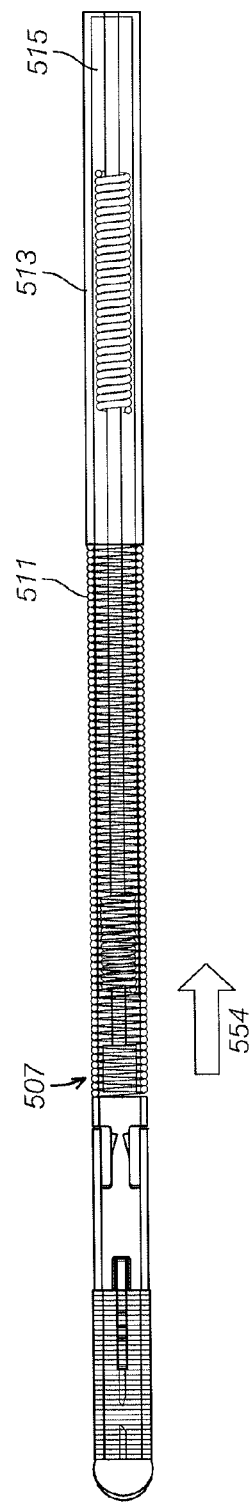

In FIG. 5B, sufficient proximal pulling force 554 has been applied to the pull wire so that the enlarged distal end of the pull wire 507 deforms the detents in the trap lumen of the hub assembly (e.g., the deformable mechanical release portion of the hub assembly). The pull wire is then retracted into the lumen of the pusher assembly; when the pull wire is coupled to the marker (e.g., 30 mm marker 513) that is visible under fluoroscopy, the release of the implant maybe immediately detected by the physician. Immediately thereafter, as shown in FIG. 5C, the implant and hub assembly 503 are separated 555 (arrow).

Figure 5C:
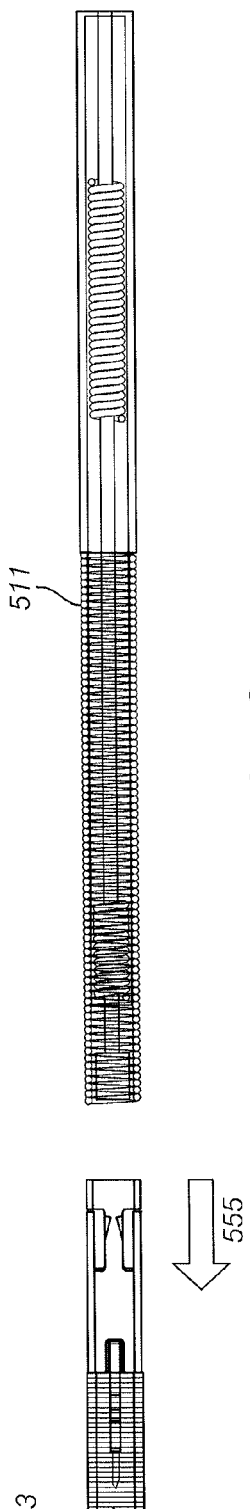
Figure 5D:
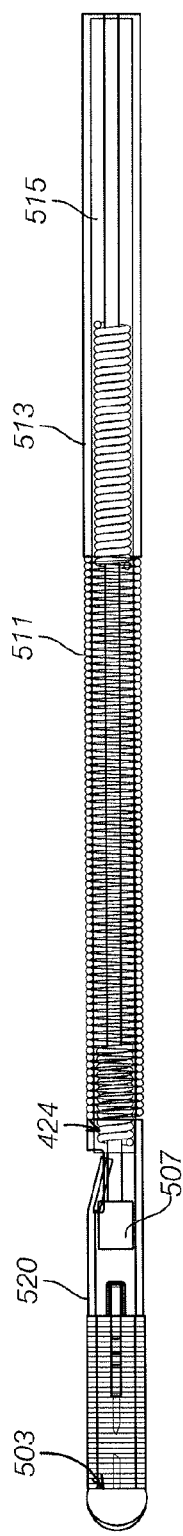
FIGS. 5D-5F illustrate actuation of another example of an apparatus similar to the one shown in FIG. 4, having a single deformable detent (tab). These images also slow the internal fluoro marker in initial (pre-detachment, FIG. 5D) and final (post detachment, FIG. 5F) positions.
Figure 5E:
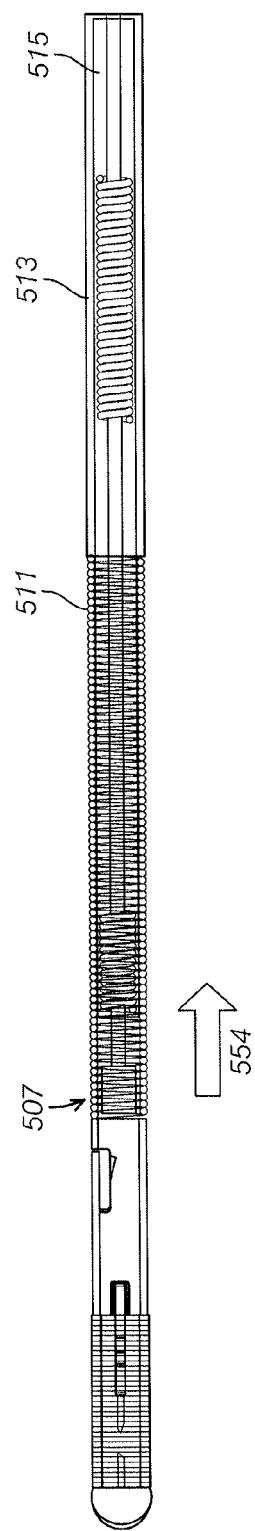
Figure 5F:
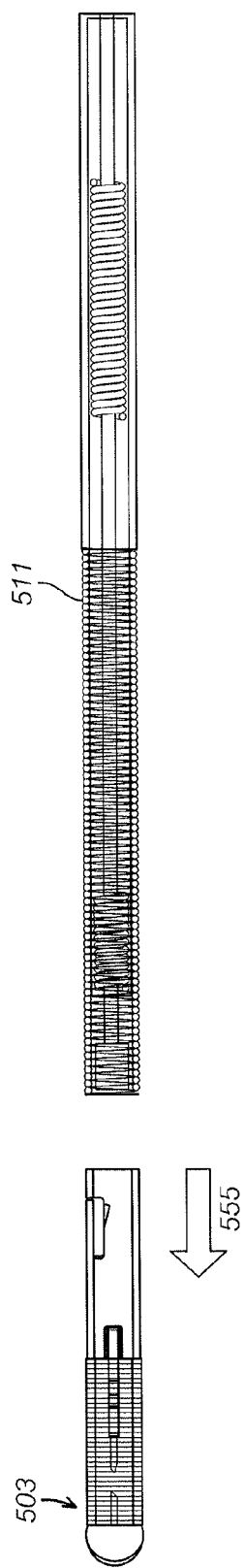

FIGS. 5D-5F illustrate another example of an apparatus similar to the apparatus shown in FIGS. 5A-5C, but including a hub assembly which only has one deformable tab 520. In general, any number of deformable tabs (deformable detents) may be used.

Figure 6A:
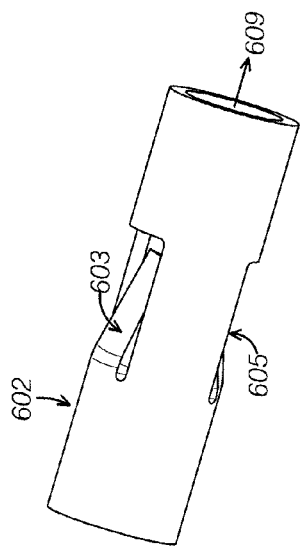
FIGS. 6A and 6B illustrate a hub body of a hub assembly (shown this example as a deformable mechanical release portion of a hub assembly) including a pair of deformable detents (shown as tabs).
Figure 6B:
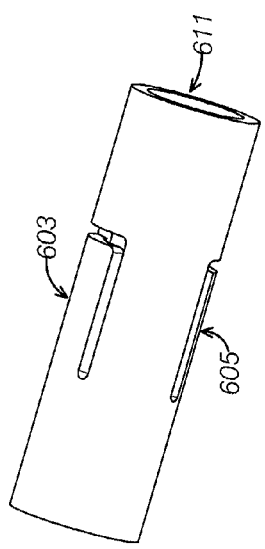

FIG. 6A shows an example of a deformable mechanical release portion of a hub assembly 602 similar to that shown above in FIGS. 5A-5C. In FIG. 6A, the deformable mechanical release portion 602 includes two deformable detents 603, 605 formed by cutting flaps out from the walls of the deformable mechanical release portion, and bending them in to trap (in the internal trap lumen) an enlarged end of the pull wire (not shown). The deformable detents in this example are oriented so that a proximal force (in the proximal direction 609) will deform the tabs back out, to the sides of the deformable mechanical release portion, as illustrated in FIG. 6B. The deformable mechanical release portion of the hub assembly includes an inner lumen that may be accessed through a proximal opening 611 into which the distal end of the pull wire may be placed.

Figure 6C:
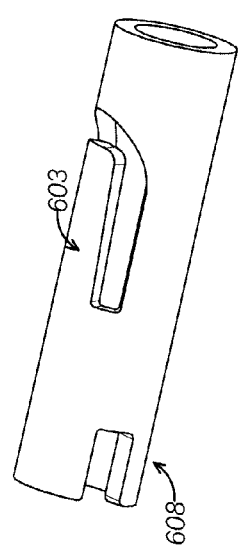
FIG. 6C is another example of a hub body of a hub assembly including a single deformable detent (tab).

Similarly, FIG. 6C shows an example of a deformable mechanical release portion of a hub assembly 608 similar to that shown in FIGS. 5A-5B, however in FIG. 5C, the deformable mechanical release portion includes only a single deformable detent 603.

Figure 7A:
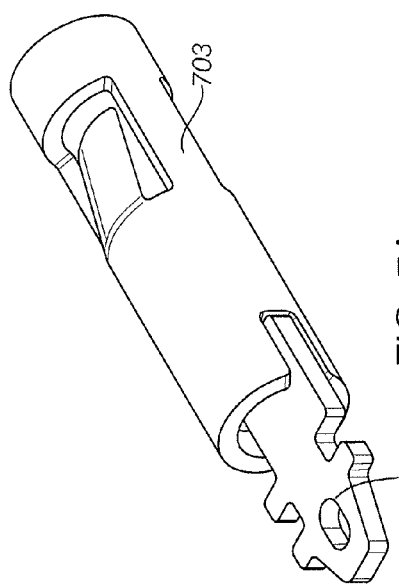
FIGS. 7A-7C illustrate perspective, side and top views, respectively, of one variation of a hub assembly, including a hub body (a deformable mechanical release portion) and an implant coupler (implant adapter).
Figure 7B:
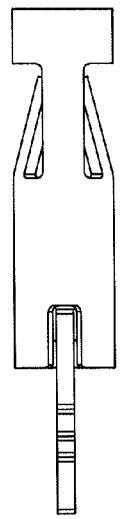
Figure 7C:
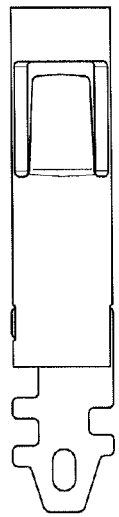

FIGS. 7A-7C illustrate different views of a hub assembly comprising a deformable mechanical release portion 703 that is affixed to an implant coupler (implant adapter) 707. In general, the two-part hub assembly may be made unitary by securing the deformable mechanical release portion 703 to the implant coupler 707, e.g., by welding, gluing, etc. An implant may be coupled to the implant coupler 707 either before or after coupling to the deformable mechanical release portion 703. As mentioned above, in some variations the hub assembly is formed of only a single piece that may perform both functions, rather than separate deformable mechanical release portion and implant coupler.

Figure 8A:
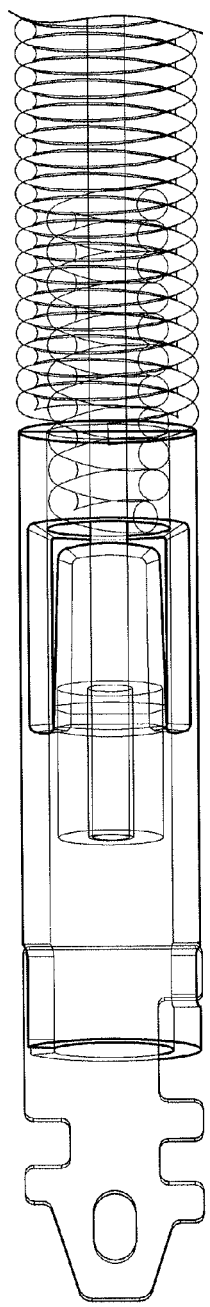
FIGS. 8A-8D illustrate top, perspective, alternative perspective, and side views, respectively, of a hub assembly (not shown connected to an implant) coupled to a DDW, including a distal end of the guidewire of the DDW.
Figure 8B:
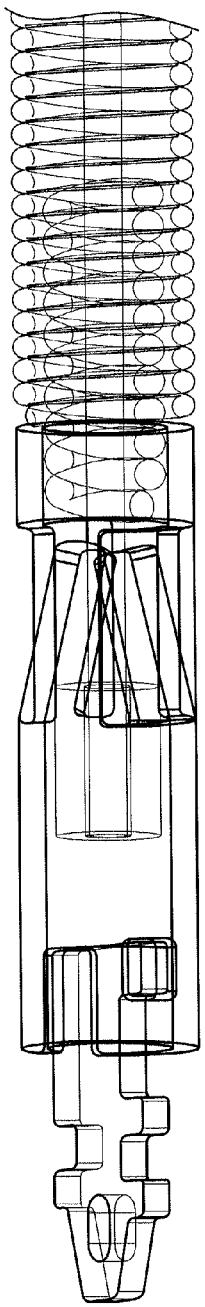
Figure 8C:
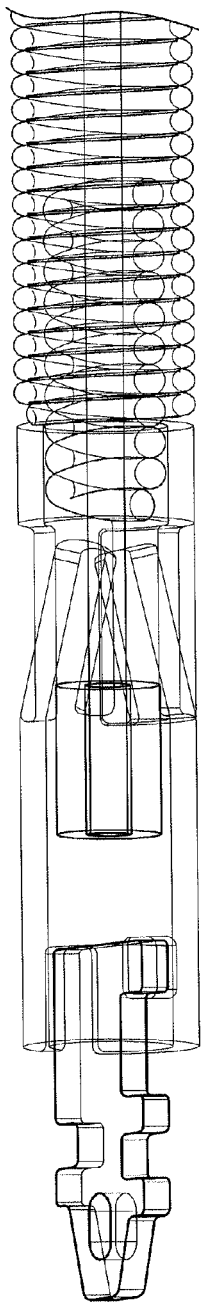
Figure 8D:
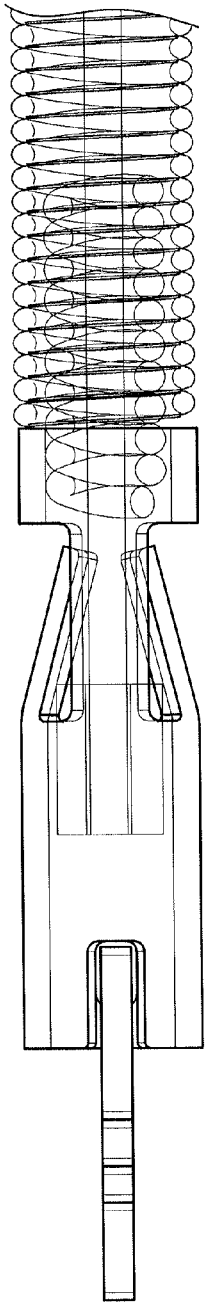

FIGS. 8A-8D illustrate a hub assembly such as the one shown in FIGS. 7A-7C coupled to the distal end of a DDW. In particular, FIG. 8C shows a partially transparent deformable mechanical release portion of the hub assembly, showing the enlarged distal end of the pull wire trapped within the trap lumen by the deformable detents.

Figure 9A:
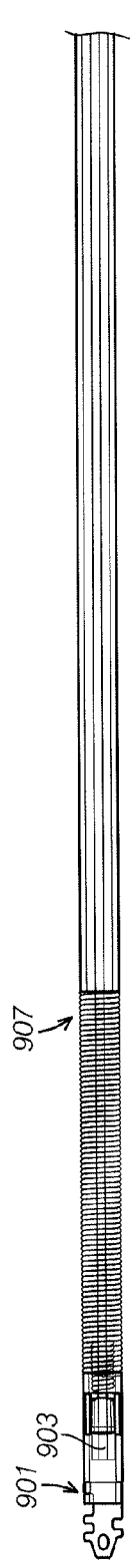
FIGS. 9A-9E show one variation of portions of an entire length of a detachable delivery wire such as the one shown in FIGS. 8A-8D coupled to a hub assembly.
Figure 9B:
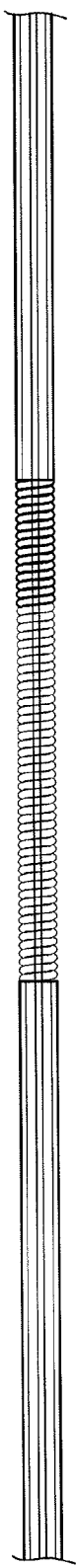
Figure 9C:
Figure 9D:
Figure 9E:
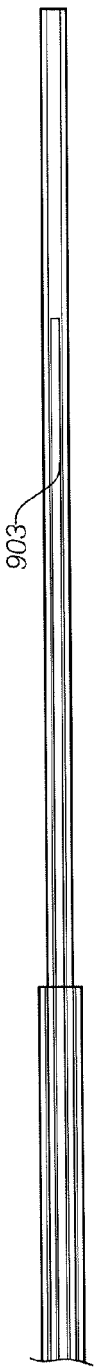

Similarly, FIGS. 9A-9E illustrate views of a single elongate apparatus, and in particular the detachable delivery wire (DDW). In FIG. 9A, a hub assembly 901 is coupled to the distal end of the pull wire 903 of the DDW. The DDW includes the inner pull wire 905 and an outer pusher assembly 907. The distal end of the pusher member includes a coil region. The proximal coil region is covered by a sleeve. The DDW may extend for region not shown between each of FIGS. 9A-9E, thus these figures do not show the full length. For example, in FIG. 9B or in the region of the pusher member extending between the regions shown in FIGS. 9A and 9B, the DDW outer region (pusher assembly or pusher) may include an outer marker (e.g., a fluoro saver marker) or visualizeable region. This marker or marker region may be positioned so that it can be easily visualized relative to the marker or markers on the pull wire within the DDW, as will be described in greater detail below (with reference to FIGS. 17A-18B). In FIG. 9C, there is a transition between the distal coil region and a more proximal hypotube (and stiffer) region 913. FIG. 9D shows a strain relief region 915 including a spring region 917 (described in greater detail below in FIGS. 10 and 10B. In this example the internal pull wire 903 may be crimped or otherwise releasably secured within the outer pusher assembly to maintain sufficient tension to keep the implant and hub assembly flush against the distal end of the apparatus.

A strain relief member such as that shown in FIGS. 9D and 10A-10B may be useful to keep the tension on the pull wire while still maintaining flexibility in the DDW so that it can be delivered as needed. For example in FIG. 10A the strain relief region 915 includes a central spring-shaped region 917 (spring region) formed of sinusoidal cutout regions of through the hypotube of the strain relief portion. This spring region 917 may allow biased compression as the tethered pull wire pulls against the body of the outer pusher assembly when bending (e.g., when passing through tortuous lumen and/or vessels of the body).

FIG. 11 shows an example of an exploded view of the distal end region of an apparatus including a hub assembly 1103, a pull wire 1105 having an enlarged diameter distal end 1107, a centering element (coil) 1109, a 30 mm fluoro marker 1117 and a lubricious polymer jacket 1120. In any of the variations described herein, a lubricious polymer jacket may reduce internal sliding friction when the pull wire is pulled proximally. A distal portion (soft coil tip portion) of an outer pusher assembly 1115 is also shown. The apparatus may be delivered to a customer assembled with an implant (not shown) connected to the hub assembly and the distal end of the pull wire engaged within the lumen trap of the hub assembly. The pull wire may be within an inner lumen of the outer pusher assembly.

FIG. 12 shows an enlarged view of an implant (in this case, a vasoocclusive coil 1203) coupled (e.g., permanently) to a hub assembly (shown here as an implant coupler/adapter portion 1205 of a hub assembly 1204 which is also connected to a deformable mechanical release 1207.

In one exemplary method of use, and introducer sheath is placed into femoral artery. A guide catheter (GC) is introduced into the introducer sheath and is navigated over guidewire to desired vascular location. A micro catheter (MC) may then be navigated over guidewire through GC to desired vascular location. The DDW/Coil within introducer may be advanced through hemostatic valve into MC hub. The DDW/Coil may then be fully advanced out of introducer into the MC, and the introducer removed from DDW. The DDW/Coil may be advanced through the MC to prepare for Implant deployment. The MC distal tip placed into desired vascular location. The coil may be deployed into desired vascular location and position verified. Optionally the coil may be retracted into MC and redeployed or removed from patient. The DH may then be attached to proximal end of DDW. The coil may be detached into desired vascular location by actuating DH. Finally, the coil position verified and need for additional Coils determined.

Figure 13A:
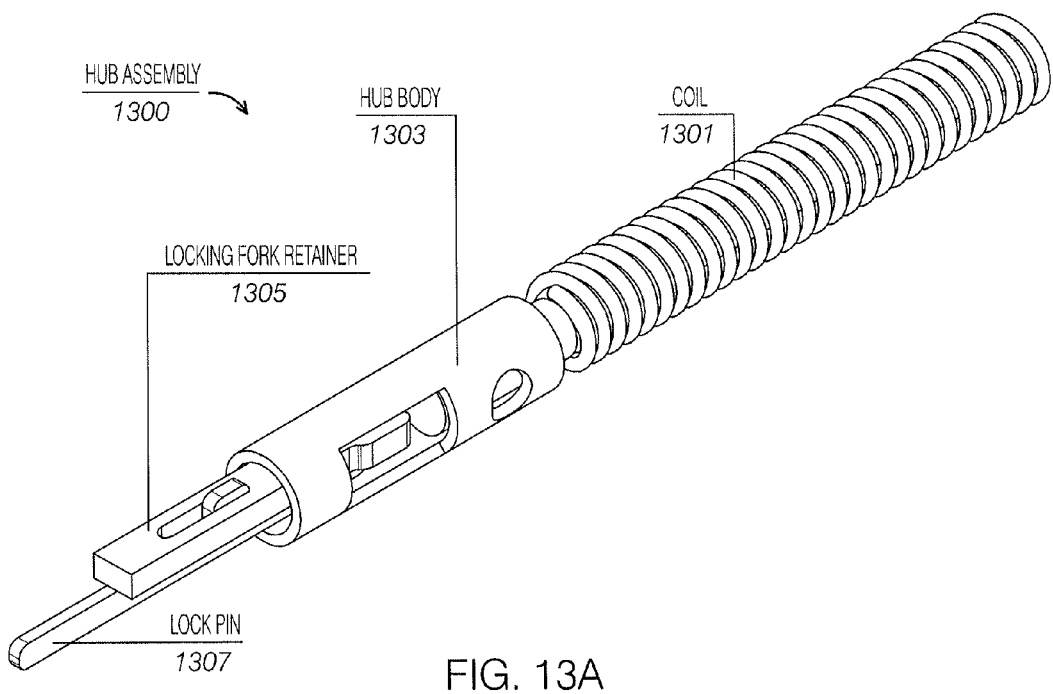
Figure 13B:
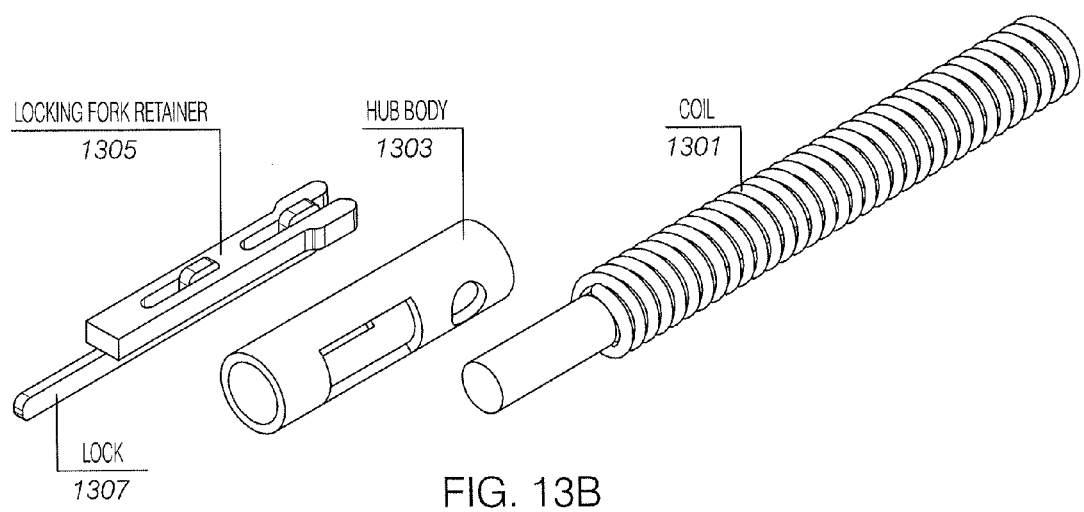
FIG. 13B is an exploded view of the apparatus of FIG. 13A.

FIGS. 13-16B illustrate another example of an apparatus as described herein. For example, FIG. 13 shows an implant (coil 1301) coupled to a hub assembly 1303, 1305, 1307 that includes a hub body 1303 that is elongate and approximately (e.g., not perfectly, or entirely enclosed) cylindrical, a locking fork retainer within the hub body, and an axial sliding lock 1307 which may couple to a pull wire of a DDW (not shown). The axial sliding lock is configured to be pulled proximally (e.g., by a pull wire) to release the locking fork retainer 1305 by deforming the tines of the locking fork retainer to release the locking fork retainer from the hub body 1303 of the hub assembly.

FIG. 14 is an exploded view of the apparatus of FIG. 13, showing the relationship between the (normally connected) coil 1303, which is connected proximally to the hub body. The hub body 1303 is connected distally to a locking fork retainer 1305 and a locking pin 1307. In FIG. 14, the component of the locking fork retainer 1305 and the locking pin 1307 may be releasably secured to prevent proximal motion of the locking pin 1307 and fork retainer 1305. For example, the locking pin 1307 may be coupled to a single pull wire (while in other variations multiple pull wires may be used, e.g., to separately release the lock and/or to pull the fork retainer 1305 proximally) that overcomes some threshold force keeping tension on the pull wire to drive the implant (coupled to the hub assembly proximally against the prior art we've already examined.

FIGS. 15A and 15B show top and side views, respectively, of the apparatus of FIG. 13. In FIG. 15A, the key and locking pin are shown arranged to take advantage of the geometry of the detachable hub 1400, including the configuration of the fork retainer 1405 when force is applied to pull it proximally (e.g., via a pull wire to which it is attached. In FIG. 15B, the locking pin 1403 has been slid proximally, and the fork retainer 1403 also slides proximally, allowing the implant (still attached to the detachment hub body) to be released. Note that, as with the embodiments described above, in this example, the tension on the pull wire may permit ejecting of the implant (and detachment hub) with sufficient force. This detachment may therefore generally eject the implant towards the implantation (target) site, such as a dilation within the neurovascular system that should be occluded. FIGS. 15A-15C illustrates this ejection.

In FIGS. 15A-15C, operation of a locking fork retainer and hub assembly such as the one shown in FIG. 13 is shown, including release of a the hub assembly (and any implant attached thereto) by moving first the locking pin 1504 and then the locking fork retainer 1503 proximally (arrows) until the tines of the locking fork deform/deflect, to release from the opening through the hub body 1501, as shown in FIG. 15C.

Figure 16A:
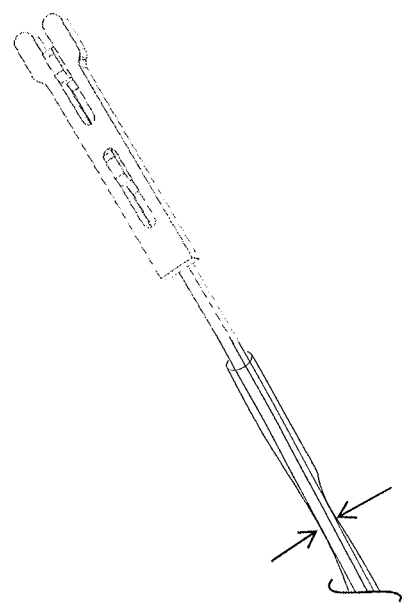
FIGS. 16A and 16B illustrate variations of the locking fork retainer and hub assembly similar to those shown in FIGS. 13A-15C.
Figure 16B:
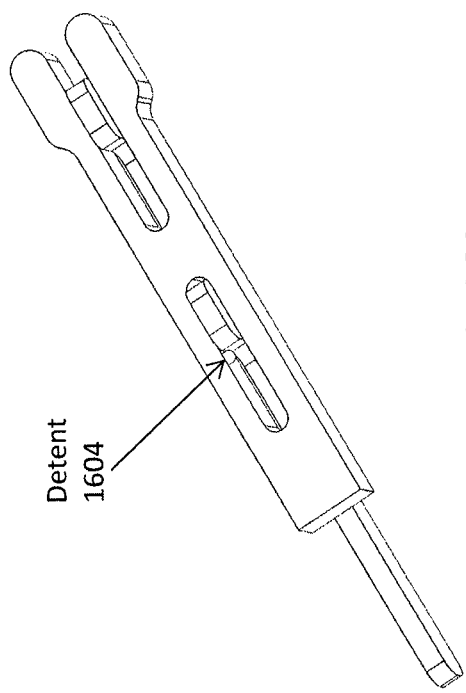

FIGS. 16A-16B illustrate variations of the locking fork retainer and hub assembly similar to those shown above, illustrating tension or friction enhancing elements against which force must be applied (e.g., by pulling the pull wire proximally) to release the locking pin and locking fork so that they may be pulled or slid proximally ad described above. For example, in FIG. 16A a detent 1604 on either the locking pin or locking fork prevents the proximal motion of the locking pin. Similarly, in FIG. 16B, a distal region of the apparatus includes a construction that, by enhanced friction, prevents the pull wire from being pulled proximally to release the locking pin and locking fork; sufficient force must be applied to the pull wire to overcome the friction 1606 in this region.

Figure 17C:
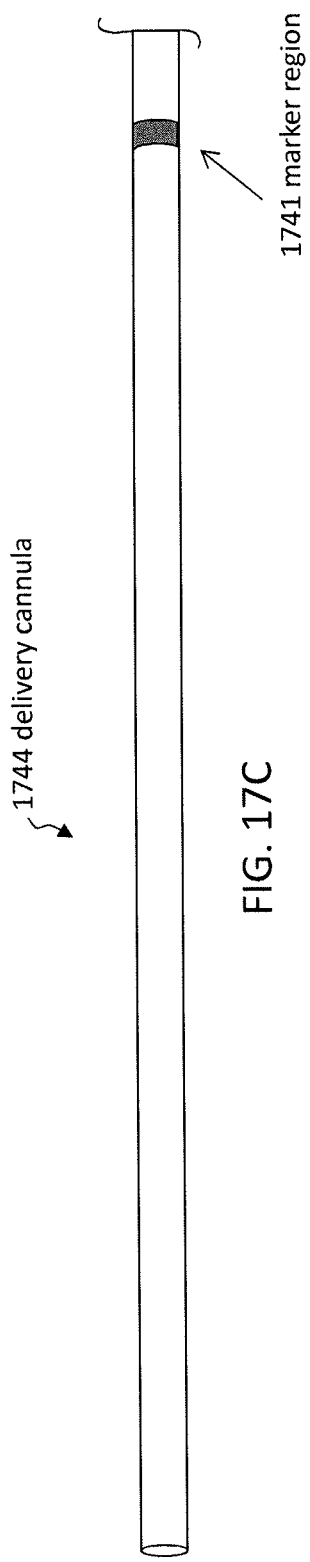
Figure 17D:
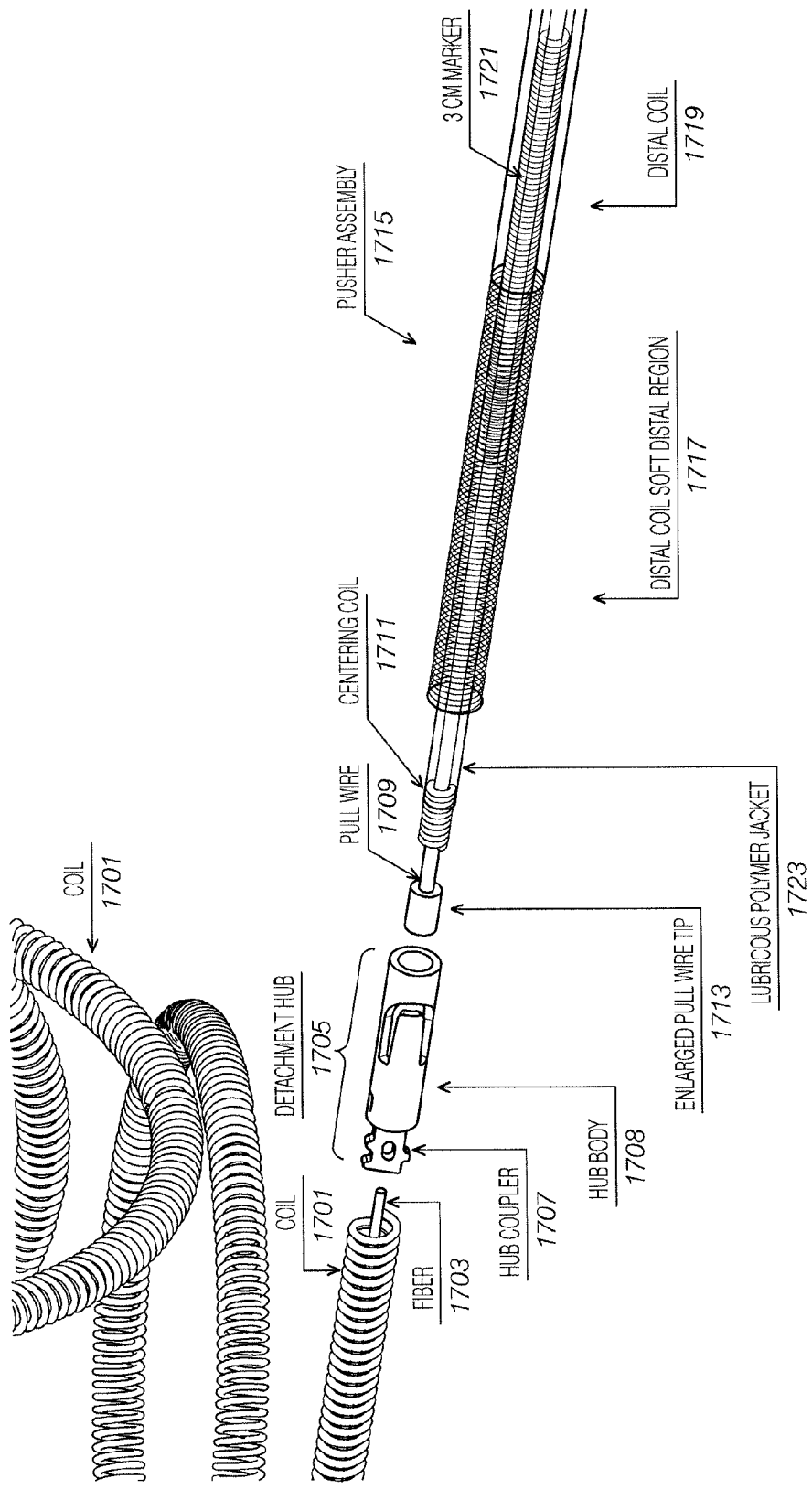
FIG. 17D is an exploded view showing the implant (coil), detachment hub and pusher assembly including the pull wire that couples to the detachment hub.

FIGS. 17A-17D illustrate another variation of a system, configured as a vascular embolization coil system, that includes: an implant comprising an embolization coil 1701; a detachment hub assembly 1705 to which the embolization coil is attached, wherein the detachment hub assembly includes one or more deformable release tabs (not visible in FIGS. 17A-17D, but see FIGS. 6A-7C, showing a similar embodiment); and a detachable delivery wire (DDW) assembly having: an outer pusher assembly 1715, and an inner pull wire 1709 having a fluoro marker 1721 attached approximately 30 mm from the distal end of the pull wire and an enlarged-diameter distal end region 1713, wherein the enlarged-diameter distal end region is held within the detachment hub by one or more deformable release tabs, further wherein the deformable release tabs are configured to be deformed and the fluoro marker moved proximally by pulling the inner pull wire proximally to release the detachment hub assembly from a distal end of the DDW assembly. In any of the apparatuses described herein, a lubricous polymer jacket may be used to cover a portion of the apparatus, such as the pull wire (e.g., the distal end region of the pull wire), centering coil and marker as shown in FIG. 17D, described below.

In FIG. 17A, the implant (coil 1701) is shown pre-loaded or attached to the hub assembly (via an implant coupler that is connected to the hub body) in these figures, and the hub assembly is held against the distal end of the DDW assembly. FIG. 17B shows a slightly enlarged view, with the coil not shown. Both FIGS. 17A and 17B show a radiopaque marker 1721 proximal to the distal end of the DDW, on the inner pull wire. Any appropriate radiopaque (e.g., visualizable under fluoroscopy) may be used. The marker may be at any appropriate position, for example, approximately 3 mm-50 mm from the distal end.

A second radiopaque marker may be positioned at a fixed location of an insertion/guide/micro catheter 1744 that may be included with (or used with) any of the system described herein. As mentioned above, a second radiopaque marker may be positioned at a fixed location along the length of the DDW (not shown) itself to coincide with the radiopaque marker on the pull wire to provide a relative position change during actuation. In FIG. 17C, the radiopaque marker 1741 is also positioned approximately 30 mm from the distal (open) end of the insertion/guide/microcatheter. The diameter of the insertion/guide/microcatheter is typically sufficient to allow passage of the apparatuses described herein, including any attached implants.

FIG. 17D shows an exploded view of the system shown in FIG. 17A, including the inner pull wire having an enlarged distal end (shown as cylindrical in this example, though other shapes, including round/spherical, oval/ovoid, rectangular, cubic, etc. may be used) and a centering coil 1711. The centering coil can alternately be an extruded polymer tube or heat shrunk onto the inner pull wire 1709. The detachment hub (including a hub body 1708 and hub coupler 1707) are also illustrated; the coil 1701 may be coupled to the hub coupler and therefore the detachment hub which may in turn releasably couple it to the delivery device (DDW). The coil may include a fiber 1703 within the coil to prevent coil elongation, helping it to maintain its shape, during manipulations including implantation.

FIGS. 18A and 18B illustrate one example of a handle that may be used with any of the apparatuses described herein, such as the systems shown in FIGS. 17A-17D. In this example, the handle includes a control (slider 1805) on the body of the handle that may be used to pull the pull the proximal end of the pull wire proximally while the handle also holds the outer pusher assembly portion (from the proximal end), to deform the tab(s) on the hub assembly and release the implant (and detachment hub) distally. FIG. 18B shows a cross-section through one example of the handle. The proximal end of the system (of the detachable delivery wire) may be inserted into the distal opening of the handle so that the inner pull wire and outer pusher assembly may be separately manipulated.

Figure 19A:
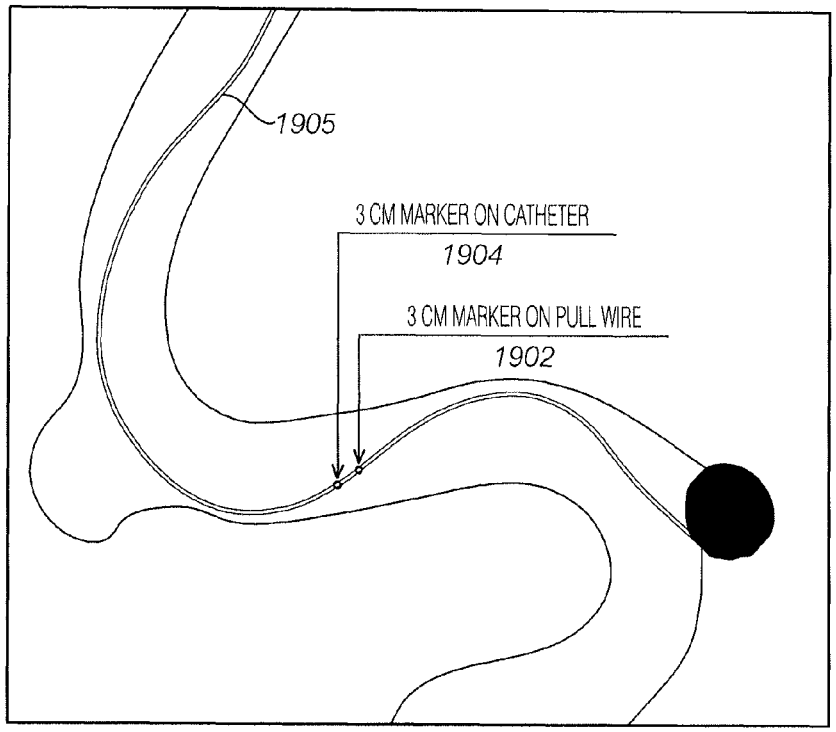
FIGS. 19A and 19B illustrate delivery of an implant using the apparatus described herein, showing a pair of fluoroscopic images of a vessel before and after controlled release of the implant as described herein. Markers on both the pull wire of the pusher assembly (DDW assembly) and the delivery catheter visually and unambiguously illustrate release of the implant.
Figure 19B:
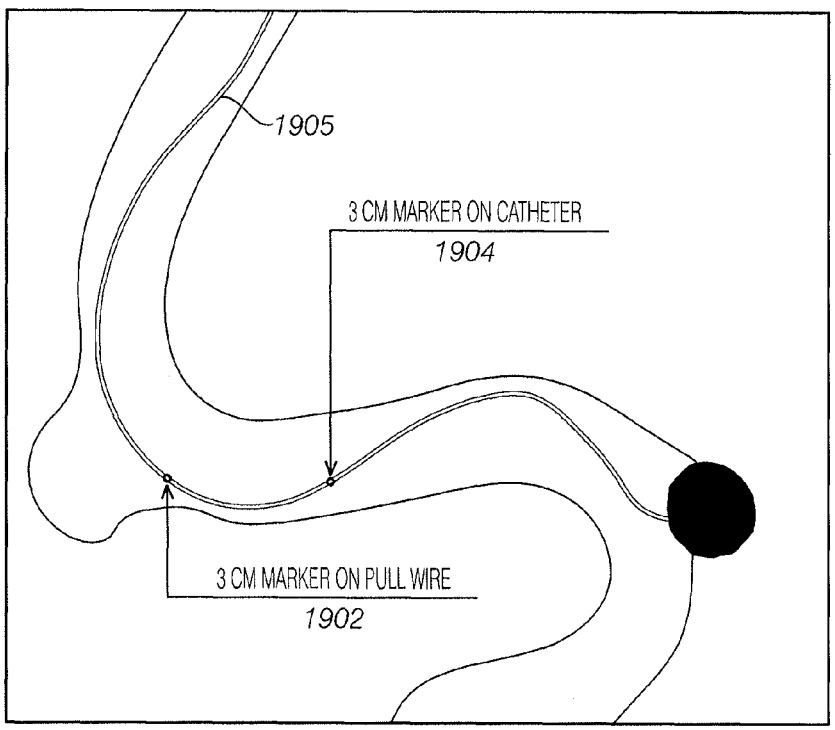

FIGS. 19A and 19B show an example of a system as described herein (e.g., in FIGS. 17A-17D) inserting an implant (coil) into a body through a vessel lumen. In this example, the system 1905 is inserted into the vessel using a microcatheter. The distal end of the microcatheter is positioned near the desired implantation site. The system, including an implant coupled to a detachment hub and through the detachment hub to distal end of a DDW can then be extended from the microcatheter so that the implant is proximate to the implantation site. Once in position, the proximal handle may be activated (or the DDW may be manually or otherwise manipulated) to pull the inner pull wire proximally, overcoming the internal resistance, and deforming the tab(s) of the detachment hub body by pulling the enlarged distal end region of the pull wire proximally against the tabs and moving the 3 cm marker proximally. Once the tab(s) deform to allow the distal end of the pull wire to pull free of the detachment body, the detachment hub and implant are released. The release may be easily and visually detected using fluoroscopy in a manner that is superior to existing systems. In this example, FIG. 19A shows the position of the system initially within the body, prior to deployment. Markers on both the pull wire 1902 of the DDW ("3 cm marker", or deployment markers, although it may be positioned at any appropriate location on the pull wire) and the guide catheter 1904 ("3 cm guide catheter" although it may be positioned at any location on the guide catheter) are visible and are positioned relatively close to each other in this example. In FIG. 19B, the pull wire has been drawn proximally with sufficient force (e.g., >20 g of force, between 20-500 g force, etc.) to detach the pull wire from the hub. The imaging (e.g. fluoroscopy) may show a quick and easily recognized change in the relative position of the pull wire maker 1902 relative to the stationary guide catheter marker 1904. Thus visual confirmation under fluoroscopy of the detachment can be seen prominently by movement, e.g. a few mm or more of movement proximally, of the pull wire marker. There may also be a tactile and/or audible component, but the visual image is easily tracked and recorded as part of the procedure log.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A vascular embolization coil system for use with a microcatheter, the system comprising:
    an implant comprising an embolization coil;
    a detachment hub assembly to which the embolization coil is attached, wherein the detachment hub assembly includes one or more deformable release tabs and an outer proximal face; and
    a detachable delivery wire (DDW) assembly having:
        an outer pusher assembly having a distal face configured to fit flush against the outer proximal face of the detachment hub assembly,
        an inner pull wire having an enlarged-diameter distal end region, wherein the enlarged-diameter distal end region is held within the detachment hub by one or more deformable release tabs, and
        a centering coil partially within the detachment hub assembly and proximal to the enlarged-diameter distal end region on the inner pull wire to keep the inner pull wire centered in the outer pusher assembly, wherein the centering coil is movable relative to the outer pusher assembly,
        further wherein the deformable release tabs are configured to be deformed by pulling the inner pull wire proximally to release the detachment hub assembly from a distal end of the DDW assembly when the distal face of the outer pusher assembly is pulled against the outer proximal face of the detachment hub.

2. The system of claim 1, further comprising a detachment handle (DH).

3. The system of claim 1, wherein the outer pusher assembly comprises an outer coil and one or more hypotubes having sufficient column strength to push the implant distally.

4. The system of claim 1, wherein the enlarged-diameter distal end region comprises a cylinder having a diameter that is greater than the diameter of a region of the inner pull wire that is proximal to the enlarged-diameter distal end region.

5. The system of claim 1, wherein the outer pusher assembly comprises a proximal strain relief region.

6. The system of claim 1, further comprising a lubricious cover at least partially over the inner pull wire.

7. The system of claim 1, wherein the inner pull wire is frictionally coupled to the outer pusher assembly to keep tension on the inner pull wire at a distal end of the DDW so that the detachment hub assembly is held against the distal end of the DDW assembly.

8. The system of claim 1, wherein the one or more deformable release tabs are configured to be deformed by pulling with greater than about 20 g of force from a proximal end of the pull wire.

9. The system of claim 1, wherein the one or more deformable release tabs are configured to be deformed by pulling with between about 20-500 g of force from a proximal end of the pull wire.

10. The system of claim 1, wherein the detachment hub assembly comprises a hub body having a proximal opening that is at least partially closed by one or more deformable release tabs and an implant coupler attached to the distal end region of the hub body, wherein the embolization coil is attached to the implant coupler.

11. A vascular embolization coil system for use with a microcatheter, the system comprising:
    an implant comprising an embolization coil;
    a detachment hub assembly to which the embolization coil is attached at a distal end, wherein the detachment hub assembly includes one or more deformable release tabs at least partially enclosing a proximal end opening and an outer proximal face;
    a detachable delivery wire (DDW) assembly having:
        an outer pusher assembly having a distal face configured to fit flush against the outer proximal face of the detachment hub assembly,
        an inner pull wire having an enlarged-diameter distal end region and a first radiopaque marker proximal to the distal end, wherein the enlarged-diameter distal end region is cylindrical;

a centering coil partially within the detachment hub assembly and proximal to the enlarged-diameter distal end region on the inner pull wire to keep the inner pull wire centered in the outer pusher assembly, wherein the centering coil is movable relative to the outer pusher assembly; and wherein the enlarged-diameter distal end region is held within the detachment hub by the one or more deformable release tabs and one or more deformable release tabs are configured to be deformed by pulling the inner pull wire proximally to release the detachment hub assembly from a distal end of the DDW assembly when the distal face of the outer pusher assembly is pulled against the outer proximal face of the detachment hub;

further wherein the release may be detected by a change in the relative positions of the first and a second radiopaque marker on the outer pusher assembly or a delivery catheter.

12. The system of claim 11, further comprising a detachment handle (DH).

13. The system of claim 11, wherein the outer pusher assembly comprises an outer coil and one or more hypotubes having sufficient column strength to push the implant distally.

14. The system of claim 11, wherein the outer pusher assembly comprises a proximal strain relief region.

15. The system of claim 11, further comprising a lubricious cover at least partially over the inner pull wire.

16. The system of claim 11, wherein the inner pull wire is frictionally coupled to the outer pusher assembly to keep tension on the inner pull wire at a distal end of the DDW so that the detachment hub assembly is held against the distal end of the DDW assembly.

17. The system of claim 11, wherein the one or more deformable release tabs are configured to be deformed by pulling with about 20 g or greater of force from a proximal end of the pull wire.

18. The system of claim 11, wherein the detachment hub assembly comprises a hub body having a proximal opening that is at least partially closed by one or more deformable release tabs and an implant coupler attached to the distal end region of the hub body, wherein the embolization coil is attached to the implant coupler.

19. A vascular embolization coil system for use with a microcatheter, the system comprising:

an implant comprising an embolization coil;

a detachment hub assembly to which the embolization coil is attached at a distal end, wherein the detachment hub assembly includes one or more deformable release tabs at least partially enclosing a proximal end opening and an outer proximal face;

a detachable delivery wire (DDW) assembly having:

an outer pusher assembly having a distal face configured to fit flush against the outer proximal face of the detachment hub assembly, an inner pull wire having an enlarged-diameter distal end region and a first radiopaque marker proximal to the distal end, wherein the enlarged-diameter distal end region is cylindrical;

a centering coil partially within the detachment hub assembly and proximal to the enlarged-diameter distal end region on the inner pull wire to keep the inner pull wire centered in the outer pusher assembly, wherein the centering coil is movable relative to the outer pusher assembly; and wherein the enlarged-diameter distal end region is held within the detachment hub by the one or more deformable release tabs and one or more deformable release tabs are configured to be deformed by pulling the inner pull wire proximally to release the detachment hub assembly from a distal end of the DDW assembly when the distal face of the outer pusher assembly is pulled against the outer proximal face of the detachment hub;

further wherein the release may be detected by a change in the relative positions of the first and a second radiopaque marker on the outer pusher assembly or a delivery catheter.

* * * * *